United States Patent [19]

Schneider et al.

[11] Patent Number: 5,538,861
[45] Date of Patent: Jul. 23, 1996

[54] DNA ENCODING A STIMULATING FACTOR FOR THE AXL RECEPTOR

[75] Inventors: Claudio Schneider, Via Tarviso No. 2, 33100 Udine, Italy; Brian C. Varnum, Los Angeles, Calif.; Giancarlo Avanzi, Novara, Italy; Claudio Brancolini; Guidalberto Manfioletti, both of Treiste, Italy

[73] Assignees: Amgen Inc., Thousand Oaks, Calif.; Claudio Schneider, Udine, Italy

[21] Appl. No.: 282,141

[22] Filed: Jul. 29, 1994

[51] Int. Cl.$^6$ .............................. C12N 15/12; C12N 1/21; C12N 5/10

[52] U.S. Cl. .................. 435/69.1; 435/252.3; 435/320.1; 435/69.4; 536/23.5

[58] Field of Search .................................. 536/23.1, 23.5, 536/24.31; 435/69.1, 69.4, 70.1, 70.3, 71.1, 71.2, 240.1, 240.2, 320.1; 530/350, 399

[56] References Cited

PUBLICATIONS

Schneider, C. et al., Cell, vol. 54, pp. 787–793 (1988).
Manfioletti, G. et al., Mol. and Cell. Biol., vol. 113, No. 8, pp. 4976–4985 (1993).
O'Bryan, J. P., et al., Mol. and Cell. Biol., vol. 11, No. 10, pp. 5016–5031 (1991).

*Primary Examiner*—Garnette D. Draper
*Assistant Examiner*—C. Saoud
*Attorney, Agent, or Firm*—Richard J. Mazza

[57] ABSTRACT

A protein which is a stimulator of and presumed ligand for the axl receptor has been identified and sequenced. The protein, termed gas6, bears homology to human protein S and is a growth factor for tissues which express axl.

7 Claims, 20 Drawing Sheets

FIG. 1A

```
  1 CCGCAGCCGC CGCCGCCGCC GCCGCCGCGA TGTGACCTTC AGGGCCGCCA
 51 GGACGGGATG ACCGGAGCCT CCGCCCCGCG GCGCCCGCTC GCCTCGGCCT
101 CCCGGGCGCT CTGACCGCGC GTCCCCGGCC CGCCATGGCC CCTTCGCTCT
151 CGCCCGGGCC CGCCGCCCTG CGCCGCGCGC CGCAGCTGCT GCTGCTGCTG
201 CTGGCCGCGG AGTGCGCGCT TGCCGCGCTG TTGCCGGCGC GCGAGGCCAC
251 GCAGTTCCTG CGGCCCAGGC AGCGCCGCGC CTTTCAGGTC TTCGAGGAGG
301 CCAAGCAGGG CCACCTGGAG AGGGAGTGCG TGGAGGAGCT GTGCAGCCGC
351 GAGGAGGCGC GGGAGGTGTT CGAGAACGAC CCCGAGACGG ATTATTTTTA
401 CCCAAGATAC TTAGACTGCA TCAACAAGTA TGGGTCTCCG TACACCAAAA
451 ACTCAGGCTT CGCCACCTGC GTGCAAAACC TGCCTGACCA GTGCACGCCC
501 AACCCCTGCG ATAGGAAGGG GACCCAAGCC TGCCAGGACC TCATGGGCAA
551 CTTCTTCTGC CTGTGTAAAG CTGGCTGGGG GGGCCGGCTC TGCGACAAAG
601 ATGTCAACGA ATGCAGCCAG GAGAACGGGG GCTGCCTCCA GATCTGCCAC
651 AACAAGCCGG GTAGCTTCCA CTGTTCCTGC CACAGCGGCT TCGAGCTCTC
701 CTCTGATGGC AGGACCTGCC AAGACATAGA CGAGTGCGCA GACTCGGAGG
751 CCTGCGGGGA GGCGCGCTGC AAGAACCTGC CGGCTCCTA CTCCTGCCTC
801 TGTGACGAGG GCTTTGCGTA CAGCTCCCAG GAGAAGGCTT GCCGAGATGT
851 GGACGAGTGT CTGCAGGGCC GCTGTGAGCA GGTCTGCGTG AACTCCCCAG
901 GGAGCTACAC CTGCCACTGT GACGGGCGTG GGGGCCTCAA GCTGTCCCAG
```

FIG. 1B

```
 951 GACATGGACA CCTGTGAGGA CATCTTGCCG TGCGTGCCCT TCAGCGTGGC
1001 CAAGAGTGTG AAGTCCTTGT ACCTGGGCCG GATGTTCAGT GGGACCCCCG
1051 TGATCCGACT GCGCTTCAAG AGGCTGCAGC CCACCAGGCT GGTAGCTGAG
1101 TTTGACTTCC GGACCTTTGA CCCCGAGGGC ATCCTCCTCT TTGCCGGAGG
1151 CCACCAGGAC AGCACCTGGA TCGTGCTGGC CCTGAGAGCC GGCCGGCTGG
1201 AGCTGCAGCT GCGCTACAAC GGTGTCGGCC GTGTCACCAG CAGCGGCCCG
1251 GTCATCAACC ATGGCATGTG GCAGACAATC TCTGTTGAGG AGCTGGCGCG
1301 GAATCTGGTC ATCAAGGTCA ACAGGGATGC TGTCATGAAA ATCGCGGTGG
1351 CCGGGGACTT GTTCCAACCG GAGCGAGGAC TGTATCATCT GAACCTGACC
1401 GTGGGAGGTA TTCCCTTCCA TGAGAAGGAC CTCGTGCAGC CTATAAACCC
1451 TCGTCTGGAT GGCTGCATGA GGAGCTGGAA CTGGCTGAAC GGAGAAGACA
1501 CCACCATCCA GGAAACGGTG AAAGTGAACA CGAGGATGCA GTGCTTCTCG
1551 GTGACGGAGA GAGGCTCTTT CTACCCCGGG AGCGGCTTCG CCTTCTACAG
1601 CCTGGACTAC ATGCGGACCC CTCTGGACGT CGGGACTGAA TCAACCTGGG
1651 AAGTAGAAGT CGTGGCTCAC ATCCGCCCAG CCGCAGACAC AGGCGTGCTG
1701 TTTGCGCTCT GGGCCCCCGA CCTCCGTGCC GTGCCTCTCT CTGTGGCACT
1751 GGTAGACTAT CACTCCACGA AGAAACTCAA GAAGCAGCTG GTGGTCCTGG
1801 CCGTGGAGCA TACGGCCTTG GCCCTAATGG AGATCAAGGT CTGCGACGGC
1851 CAAGAGCACG TGGTCACCGT CTCGCTGAGG GACGGTGAGG CCACCCTGGA
1901 GGTGGACGGC ACCAGGGGCC AGAGCGAGGT GAGCGCCGCG CAGCTGCAGG
1951 AGAGGCTGGC CGTGCTCGAG AGGCACCTGC GGAGCCCCGT GCTCACCTTT
```

FIG. 1C

```
2001  GCTGGCGGCC TGCCAGATGT GCCGGTGACT TCAGCGCCAG TCACCGCGTT

2051  CTACCGCGGC TGCATGACAC TGGAGGTCAA CCGGAGGCTG CTGGACCTGG

2101  ACGAGGCGGC GTACAAGCAC AGCGACATCA CGGCCCACTC CTGCCCCCCC

2151  GTGGAGCCCG CCGCAGCCTA GGCCCCACG GGACGCGGCA GGCTTCTCAG

2201  TCTCTGTCCG AGACAGCCGG GAGGAGCCTG GGGGCTCCTC ACCACGTGGG

2251  GCCATGCTGA GAGCTGGGCT TTCCTCTGTG ACCATCCCGG CCTGTAACAT

2301  ATCTGTAAAT AGTGAGATGG ACTTGGGGCC TCTGACGCCG CGCACTCAGC

2351  CGTGGGCCCG GGCGCGGGA GGCCGGCGCA GCGCAGAGCG GGCTCGAAGA

2401  AAATAATTCT CTATTATTTT TATTACCAAG CGCTTCTTTC TGACTCTAAA

2451  ATATGGAAAA T
```

```
mGas6    1 ---MPPPPGPAA-ALGTALLLLLLASESSHTVLLRAREAAQFLRPRQRRAYQVFEEAKQ
hGas6    1 MAPSLSPGPAA-ALAAALRRAPQLPARAEATQFLRPRQRRAFQVFEEAKQ
hProtS   1 ---MRVLGGRCGALLACLLLVLPVSEANFLSKQQASQVLV-RKRRANSLLEETKQ mGas6      GHLERECVEEVCSKEEAREVFENDPETEYFY
hGas6      GHLERECVEELCSREEAREVFENDPETDYFY
hProtS     GNLERECIEELCNKEEAREVFENDPETDYFY
```

FIG.2C

```
mGas6   87 PRYQECMRKY-----GRPEEKNPDFAKCVQNLP
hGas6   90 PRYLDCINKY-----GSPYTKNSGEATCVQNLP
hProtS  83 PKYLVCLRSFQTGLFTAARQSTNAYPDLRSCVNAIP
```

FIG. 2D

```
mGas6  115 DQCTPNPCDKKGTHICQDLMGNFFCVCTDGWGGRLCDK
hGas6  118 DQCTPNPCDRKGTQACQDLMGNFFCLCKAGWGGRLCDK
hProtS 119 DQCSPLPCNEDGYMSCKDGKASETCTCKPGWQGEKCEF mGas6      DVNECVQK--NGGCSQVCHNKPGSFQCACHSGFSLASDGQTCQ
hGas6      DVNECSQE--NGGCLQICHNKPGSFHCSCHSGFELSDGRTCQ
hProtS     DINECKDPSNINGGCSQICDNTPGSYHCSCKNGFVMLSNKKDCK mGas6      DIDECT-DSDTCGDARCKNLPGSYSCLCDEGYTYSSKEKTCQ
hGas6      DIDECA-DSEACGEARCKNLPGSYSCLCDEGFAYSSQEKACR
hProtS     DVDECSLKPSICGTAVCKNIPGDFECECPEGYRYNLKSKSCE mGas6      DVDECQQDRCEQTCVNSPGSYTCHCDGRGGLKLSPDMDTCE
hGas6      DVDECLQGRCEQLCVNSPGSYTCHCDGRGGLKLSQDMDTCE
hProtS     DIDECSENMCAQLCVNYPGGYTCYCDGKKGFKLAQDQKSCE
```

FIG. 2E

| | | |
|---|---|---|
| mGas6 276 | DILPCVPFSMAKSVKSLYLGRMFSGTPVIRLRFKRLQPTRLLAEFDERTFDPEGVIFF |
| hGas6 279 | DILPCVPFSVAKSVKSLYLGRMFSGTPVIRLRFKRLQPTRLVAEFDERTFDPEGILLE |
| hProtS 284 | VVSVCLPLNLDTKYELYLAEQFAGV-VLYLKERLPEISRFSAEFDFRITYDSEGVILY |

| | |
|---|---|
| mGas6 | AGGRSDSTWIVLGLRAGRLELQLRYNGVGRITSSGPTINHGMWQTISVEELERNLVIK |
| hGas6 | AGGHQDSTWIVLALRAGRLELQLRYNGVGRVTSSGPVINHGMWQTISVEELARNLVIK |
| hProtS | AESIDHSAWLLIALRGGKIEVQLKNEHTSKITTGGDVINNGLWNMVSVEELEHSISIK |

| | |
|---|---|
| mGas6 | VNKDAVMKIAVAGELFQLERGLYHLNLTVGGIPKESELVQPINPRLDGCMRSWNWL |
| hGas6 | VNRDAVMKIAVAGDLFQPERGLYHLNLTVGGIPHEQDLVQPINPRLDGCMRSWNWL |
| hProtS | IAKEAVMDHNKPGPLFKPENGLETKVYFAGFPRKVESELIKPINPRLDGCIRSWNLM |

| | |
|---|---|
| mGas6 | NGEDSAIQETVKANTKMQCFSVTERGSFFPGNGFATYRLNYTRTSLDVGTETTWEVKV |
| hGas6 | NGEDTTIQETVKVNTRMQCFSVIERGSFYPGSGFAFYSLDYMDY----NNVSAEGWHV |
| hProtS | KQGASGIKEIIQEKQNKHLVTVEKGSYYPGSGIAQFHID-----NNVSSAEGWHVN |

| | |
|---|---|
| mGas6 | VARIRPATDTGVLHAL--VGDDDVVISVALVDYHSTKKLKKQLVVLAVEDVALAMEI |
| hGas6 | VAHIRPAADTGVLFALWAPDLRAVPLSLVVLAVEHTALALMEI |
| hProtS | TLNIRPSTGTGVMLAL--VSGNNTVPFAVSLVD--ST-SEKSQDILLSVE-NTVIYRIQ |

| | |
|---|---|
| mGas6 | KVCDSQEHTVTVSLREGEATLEVDGTKGQSEVSTAQLQERLDTLKTHLQGSVHTYVGG |
| hGas6 | KVCDGQEHVVTVSLRDGEATLEVDGTRGQSEVSAAQLQERLAVLERHLRSPVLTAGG |
| hProtS | ALSLCSDQQSHLEFRVNRNLELSTPLKIETISHEDLQRQLAVLDKAMKAKVATEPAAA |

| | |
|---|---|
| mGas6 | LPEVSVIISAPVTAFYRGCMTLEVNGKILDLDTASYKHSDITSHSCPPVEHATP |
| hGas6 | LPDVPVTISAPVTAFYRGCMTLEVNRRLLDLDEAAYKHSDITAHSCPPVEPAAA |
| hProtS | LPDVPFSATPVNAFYNGCMEVNINGCMEVNINGVQLDLDEAISKKHNDIRAHSCPSVWKKTKNS |

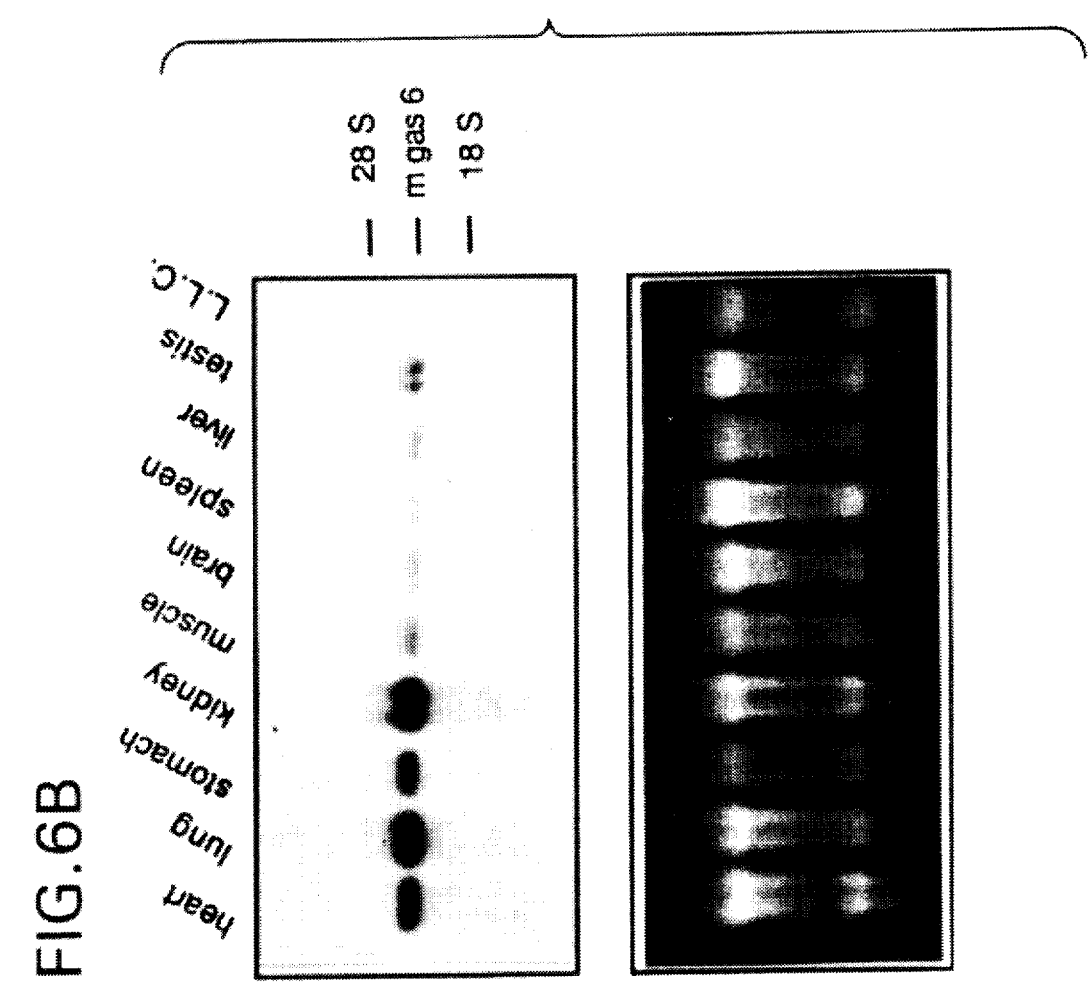

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2461 base pairs
        ( B ) TYPE: nucleic acid
        ( C ) STRANDEDNESS: unknown
        ( D ) TOPOLOGY: unknown ( i i ) MOLECULE TYPE: cDNA ( x i ) SEQUENCE DESCRIPTION: SEQ ID NO:1:

```
CCGCAGCCGC  CGCCGCCGCC  GCCGCCGCGA  TGTGACCTTC  AGGGCCGCCA  GGACGGGATG      60

ACCGGAGCCT  CCGCCCCGCG  GCGCCCGCTC  GCCTCGGCCT  CCCGGGCGCT  CTGACCGCGC     120

GTCCCCGGCC  CGCCATGGCC  CCTTCGCTCT  CGCCCGGGCC  CGCCGCCCTG  CGCCGCGCGC     180

CGCAGCTGCT  GCTGCTGCTG  CTGGCCGCGG  AGTGCGCGCT  TGCCGCGCTG  TTGCCGGCGC     240

GCGAGGCCAC  GCAGTTCCTG  CGGCCCAGGC  AGCGCCGCGC  CTTTCAGGTC  TTCGAGGAGG     300

CCAAGCAGGG  CCACCTGGAG  AGGGAGTGCG  TGGAGGAGCT  GTGCAGCCGC  GAGGAGGCGC     360
```

-continued

| | | | | | | |
|---|---|---|---|---|---|---|
| GGGAGGTGTT | CGAGAACGAC | CCCGAGACGG | ATTATTTTTA | CCCAAGATAC | TTAGACTGCA | 420 |
| TCAACAAGTA | TGGGTCTCCG | TACACCAAAA | ACTCAGGCTT | CGCCACCTGC | GTGCAAAACC | 480 |
| TGCCTGACCA | GTGCACGCCC | AACCCCTGCG | ATAGGAAGGG | GACCCAAGCC | TGCCAGGACC | 540 |
| TCATGGGCAA | CTTCTTCTGC | CTGTGTAAAG | CTGGCTGGGG | GGGCCGGCTC | TGCGACAAAG | 600 |
| ATGTCAACGA | ATGCAGCCAG | GAGAACGGGG | GCTGCCTCCA | GATCTGCCAC | AACAAGCCGG | 660 |
| GTAGCTTCCA | CTGTTCCTGC | CACAGCGGCT | TCGAGCTCTC | CTCTGATGGC | AGGACCTGCC | 720 |
| AAGACATAGA | CGAGTGCGCA | GACTCGGAGG | CCTGCGGGGA | GGCGCGCTGC | AAGAACCTGC | 780 |
| CCGGCTCCTA | CTCCTGCCTC | TGTGACGAGG | GCTTTGCGTA | CAGCTCCCAG | GAGAAGGCTT | 840 |
| GCCGAGATGT | GGACGAGTGT | CTGCAGGGCC | GCTGTGAGCA | GGTCTGCGTG | AACTCCCCAG | 900 |
| GGAGCTACAC | CTGCCACTGT | GACGGGCGTG | GGGGCCTCAA | GCTGTCCCAG | GACATGGACA | 960 |
| CCTGTGAGGA | CATCTTGCCG | TGCGTGCCCT | TCAGCGTGGC | CAAGAGTGTG | AAGTCCTTGT | 1020 |
| ACCTGGGCCG | GATGTTCAGT | GGGACCCCCG | TGATCCGACT | GCGCTTCAAG | AGGCTGCAGC | 1080 |
| CCACCAGGCT | GGTAGCTGAG | TTTGACTTCC | GGACCTTTGA | CCCCGAGGGC | ATCCTCCTCT | 1140 |
| TTGCCGGAGG | CCACCAGGAC | AGCACCTGGA | TCGTGCTGGC | CCTGAGAGCC | GGCCGGCTGG | 1200 |
| AGCTGCAGCT | GCGCTACAAC | GGTGTCGGCC | GTGTCACCAG | CAGCGGCCCG | GTCATCAACC | 1260 |
| ATGGCATGTG | GCAGACAATC | TCTGTTGAGG | AGCTGGCGCG | GAATCTGGTC | ATCAAGGTCA | 1320 |
| ACAGGGATGC | TGTCATGAAA | ATCGCGGTGG | CCGGGGACTT | GTTCCAACCG | GAGCGAGGAC | 1380 |
| TGTATCATCT | GAACCTGACC | GTGGGAGGTA | TTCCCTTCCA | TGAGAAGGAC | CTCGTGCAGC | 1440 |
| CTATAAACCC | TCGTCTGGAT | GGCTGCATGA | GGAGCTGGAA | CTGGCTGAAC | GGAGAAGACA | 1500 |
| CCACCATCCA | GGAAACGGTG | AAAGTGAACA | CGAGGATGCA | GTGCTTCTCG | GTGACGGAGA | 1560 |
| GAGGCTCTTT | CTACCCCGGG | AGCGGCTTCG | CCTTCTACAG | CCTGGACTAC | ATGCGGACCC | 1620 |
| CTCTGGACGT | CGGGACTGAA | TCAACCTGGG | AAGTAGAAGT | CGTGGCTCAC | ATCCGCCCAG | 1680 |
| CCGCAGACAC | AGGCGTGCTG | TTTGCGCTCT | GGGCCCCCGA | CCTCCGTGCC | GTGCCTCTCT | 1740 |
| CTGTGGCACT | GGTAGACTAT | CACTCCACGA | AGAAACTCAA | GAAGCAGCTG | GTGGTCCTGG | 1800 |
| CCGTGGAGCA | TACGGCCTTG | GCCCTAATGG | AGATCAAGGT | CTGCGACGGC | CAAGAGCACG | 1860 |
| TGGTCACCGT | CTCGCTGAGG | GACGGTGAGG | CCACCCTGGA | GGTGGACGGC | ACCAGGGGCC | 1920 |
| AGAGCGAGGT | GAGCGCCGCG | CAGCTGCAGG | AGAGGCTGGC | CGTGCTCGAG | AGGCACCTGC | 1980 |
| GGAGCCCCGT | GCTCACCTTT | GCTGGCGGCC | TGCCAGATGT | GCCGGTGACT | TCAGCGCCAG | 2040 |
| TCACCGCGTT | CTACCGCGGC | TGCATGACAC | TGGAGGTCAA | CCGGAGGCTG | CTGGACCTGG | 2100 |
| ACGAGGCGGC | GTACAAGCAC | AGCGACATCA | CGGCCCACTC | CTGCCCCCCC | GTGGAGCCCG | 2160 |
| CCGCAGCCTA | GGCCCCCACG | GGACGCGGCA | GGCTTCTCAG | TCTCTGTCCG | AGACAGCCGG | 2220 |
| GAGGAGCCTG | GGGGCTCCTC | ACCACGTGGG | GCCATGCTGA | GAGCTGGGCT | TTCCTCTGTG | 2280 |
| ACCATCCCGG | CCTGTAACAT | ATCTGTAAAT | AGTGAGATGG | ACTTGGGGCC | TCTGACGCCG | 2340 |
| CGCACTCAGC | CGTGGGCCCG | GGCGCGGGGA | GGCCGGCGCA | GCGCAGAGCG | GGCTCGAAGA | 2400 |
| AAATAATTCT | CTATTATTTT | TATTACCAAG | CGCTTCTTTC | TGACTCTAAA | ATATGGAAAA | 2460 |
| T | | | | | | 2461 |

( 2 ) INFORMATION FOR SEQ ID NO:2:

( i ) SEQUENCE CHARACTERISTICS:
( A ) LENGTH: 678 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:2:

```
Met Ala Pro Ser Leu Ser Pro Gly Pro Ala Ala Leu Arg Arg Ala Pro
  1               5                  10                  15

Gln Leu Leu Leu Leu Leu Ala Ala Glu Cys Ala Leu Ala Ala Leu
            20                  25                  30

Leu Pro Ala Arg Glu Ala Thr Gln Phe Leu Arg Pro Arg Gln Arg Arg
        35                  40                  45

Ala Phe Gln Val Phe Glu Glu Ala Lys Gln Gly His Leu Glu Arg Glu
    50                  55                  60

Cys Val Glu Glu Leu Cys Ser Arg Glu Glu Ala Arg Glu Val Phe Glu
 65                  70                  75                  80

Asn Asp Pro Glu Thr Asp Tyr Phe Tyr Pro Arg Tyr Leu Asp Cys Ile
                85                  90                  95

Asn Lys Tyr Gly Ser Pro Tyr Thr Lys Asn Ser Gly Phe Ala Thr Cys
            100                 105                 110

Val Gln Asn Leu Pro Asp Gln Cys Thr Pro Asn Pro Cys Asp Arg Lys
        115                 120                 125

Gly Thr Gln Ala Cys Gln Asp Leu Met Gly Asn Phe Phe Cys Leu Cys
    130                 135                 140

Lys Ala Gly Trp Gly Gly Arg Leu Cys Asp Lys Asp Val Asn Glu Cys
145                 150                 155                 160

Ser Gln Glu Asn Gly Gly Cys Leu Gln Ile Cys His Asn Lys Pro Gly
                165                 170                 175

Ser Phe His Cys Ser Cys His Ser Gly Phe Glu Leu Ser Ser Asp Gly
            180                 185                 190

Arg Thr Cys Gln Asp Ile Asp Glu Cys Ala Asp Ser Glu Ala Cys Gly
        195                 200                 205

Glu Ala Arg Cys Lys Asn Leu Pro Gly Ser Tyr Ser Cys Leu Cys Asp
210                 215                 220

Glu Gly Phe Ala Tyr Ser Ser Gln Glu Lys Ala Cys Arg Asp Val Asp
225                 230                 235                 240

Glu Cys Leu Gln Gly Arg Cys Glu Gln Val Cys Val Asn Ser Pro Gly
                245                 250                 255

Ser Tyr Thr Cys His Cys Asp Gly Arg Gly Gly Leu Lys Leu Ser Gln
            260                 265                 270

Asp Met Asp Thr Cys Glu Asp Ile Leu Pro Cys Val Pro Phe Ser Val
        275                 280                 285

Ala Lys Ser Val Lys Ser Leu Tyr Leu Gly Arg Met Phe Ser Gly Thr
290                 295                 300

Pro Val Ile Arg Leu Arg Phe Lys Arg Leu Gln Pro Thr Arg Leu Val
305                 310                 315                 320

Ala Glu Phe Asp Phe Arg Thr Phe Asp Pro Glu Gly Ile Leu Leu Phe
                325                 330                 335

Ala Gly Gly His Gln Asp Ser Thr Trp Ile Val Leu Ala Leu Arg Ala
            340                 345                 350

Gly Arg Leu Glu Leu Gln Leu Arg Tyr Asn Gly Val Gly Arg Val Thr
        355                 360                 365

Ser Ser Gly Pro Val Ile Asn His Gly Met Trp Gln Thr Ile Ser Val
370                 375                 380

Glu Glu Leu Ala Arg Asn Leu Val Ile Lys Val Asn Arg Asp Ala Val
385                 390                 395                 400
```

-continued

| | | | | | | | | | | | | | | |
|---|---|---|---|---|---|---|---|---|---|---|---|---|---|---|
| Met | Lys | Ile | Ala | Val 405 | Ala | Gly | Asp | Leu | Phe 410 | Gln | Pro | Glu | Arg | Gly 415 | Leu |
| Tyr | His | Leu | Asn 420 | Leu | Thr | Val | Gly | Gly 425 | Ile | Pro | Phe | His | Glu 430 | Lys | Asp |
| Leu | Val | Gln 435 | Pro | Ile | Asn | Pro 440 | Arg | Leu | Asp | Gly | Cys | Met 445 | Arg | Ser | Trp |
| Asn | Trp 450 | Leu | Asn | Gly | Glu | Asp 455 | Thr | Thr | Ile | Gln | Glu 460 | Thr | Val | Lys | Val |
| Asn 465 | Thr | Arg | Met | Gln | Cys 470 | Phe | Ser | Val | Thr | Glu 475 | Arg | Gly | Ser | Phe | Tyr 480 |
| Pro | Gly | Ser | Gly | Phe 485 | Ala | Phe | Tyr | Ser | Leu 490 | Asp | Tyr | Met | Arg | Thr 495 | Pro |
| Leu | Asp | Val | Gly 500 | Thr | Glu | Ser | Thr | Trp 505 | Glu | Val | Glu | Val | Val 510 | Ala | His |
| Ile | Arg | Pro 515 | Ala | Ala | Asp | Thr | Gly 520 | Val | Leu | Phe | Ala | Leu 525 | Trp | Ala | Pro |
| Asp | Leu 530 | Arg | Ala | Val | Pro | Leu 535 | Ser | Val | Ala | Leu | Val 540 | Asp | Tyr | His | Ser |
| Thr 545 | Lys | Lys | Leu | Lys | Lys 550 | Gln | Leu | Val | Val | Leu 555 | Ala | Val | Glu | His | Thr 560 |
| Ala | Leu | Ala | Leu | Met 565 | Glu | Ile | Lys | Val | Cys 570 | Asp | Gly | Gln | Glu | His 575 | Val |
| Val | Thr | Val | Ser 580 | Leu | Arg | Asp | Gly | Glu 585 | Ala | Thr | Leu | Glu | Val 590 | Asp | Gly |
| Thr | Arg | Gly 595 | Gln | Ser | Glu | Val | Ser 600 | Ala | Ala | Gln | Leu | Gln 605 | Glu | Arg | Leu |
| Ala | Val 610 | Leu | Glu | Arg | His | Leu 615 | Arg | Ser | Pro | Val | Leu 620 | Thr | Phe | Ala | Gly |
| Gly 625 | Leu | Pro | Asp | Val | Pro 630 | Val | Thr | Ser | Ala | Pro 635 | Val | Thr | Ala | Phe | Tyr 640 |
| Arg | Gly | Cys | Met | Thr 645 | Leu | Glu | Val | Asn | Arg 650 | Arg | Leu | Leu | Asp | Leu 655 | Asp |
| Glu | Ala | Ala | Tyr 660 | Lys | His | Ser | Asp | Ile 665 | Thr | Ala | His | Ser | Cys 670 | Pro | Pro |
| Val | Glu | Pro 675 | Ala | Ala | Ala | | | | | | | | | | |

( 2 ) INFORMATION FOR SEQ ID NO:3:

( i ) SEQUENCE CHARACTERISTICS:
        ( A ) LENGTH: 673 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met 1 | Pro | Pro | Pro | Pro 5 | Gly | Pro | Ala | Ala | Ala 10 | Leu | Gly | Thr | Ala | Leu 15 | Leu |
| Leu | Leu | Leu | Leu 20 | Ala | Ser | Glu | Ser | Ser 25 | His | Thr | Val | Leu | Leu 30 | Arg | Ala |
| Arg | Glu | Ala 35 | Ala | Gln | Phe | Leu | Arg 40 | Pro | Arg | Gln | Arg | Arg 45 | Ala | Tyr | Gln |
| Val | Phe 50 | Glu | Glu | Ala | Lys | Gln 55 | Gly | His | Leu | Glu | Arg 60 | Glu | Cys | Val | Glu |
| Glu | Val | Cys | Ser | Lys | Glu | Glu | Ala | Arg | Glu | Val | Phe | Glu | Asn | Asp | Pro |

|     |     |     |     | 65  |     |     |     | 70  |     |     |     | 75  |     |     |     | 80  |
| --- | --- | --- | --- | --- | --- | --- | --- | --- | --- | --- | --- | --- | --- | --- | --- | --- |
| Glu | Thr | Glu | Tyr | Phe | Tyr | Pro | Arg | Tyr | Gln | Glu | Cys | Met | Arg | Lys | Tyr |
|     |     |     |     | 85  |     |     |     | 90  |     |     |     | 95  |     |     |     |
| Gly | Arg | Pro | Glu | Glu | Lys | Asn | Pro | Asp | Phe | Ala | Lys | Cys | Val | Gln | Asn |
|     |     |     | 100 |     |     |     | 105 |     |     |     |     | 110 |     |     |     |
| Leu | Pro | Asp | Gln | Cys | Thr | Pro | Asn | Pro | Cys | Asp | Lys | Lys | Gly | Thr | His |
|     |     | 115 |     |     |     | 120 |     |     |     |     | 125 |     |     |     |     |
| Ile | Cys | Gln | Asp | Leu | Met | Gly | Asn | Phe | Phe | Cys | Val | Cys | Thr | Asp | Gly |
|     | 130 |     |     |     | 135 |     |     |     |     | 140 |     |     |     |     |     |
| Trp | Gly | Gly | Arg | Leu | Cys | Asp | Lys | Asp | Val | Asn | Glu | Cys | Val | Gln | Lys |
| 145 |     |     |     | 150 |     |     |     | 155 |     |     |     |     |     | 160 |     |
| Asn | Gly | Gly | Cys | Ser | Gln | Val | Cys | His | Asn | Lys | Pro | Gly | Ser | Phe | Gln |
|     |     |     | 165 |     |     | 170 |     |     |     |     |     |     |     | 175 |     |
| Cys | Ala | Cys | His | Ser | Gly | Phe | Ser | Leu | Ala | Ser | Asp | Gly | Gln | Thr | Cys |
|     |     |     | 180 |     |     |     | 185 |     |     |     |     | 190 |     |     |     |
| Gln | Asp | Ile | Asp | Glu | Cys | Thr | Asp | Ser | Asp | Thr | Cys | Gly | Asp | Ala | Arg |
|     |     | 195 |     |     |     | 200 |     |     |     |     |     | 205 |     |     |     |
| Cys | Lys | Asn | Leu | Pro | Gly | Ser | Tyr | Ser | Cys | Leu | Cys | Asp | Glu | Gly | Tyr |
|     | 210 |     |     |     | 215 |     |     |     |     | 220 |     |     |     |     |     |
| Thr | Tyr | Ser | Ser | Lys | Glu | Lys | Thr | Cys | Gln | Asp | Val | Asp | Glu | Cys | Gln |
| 225 |     |     |     | 230 |     |     |     | 235 |     |     |     |     |     | 240 |     |
| Gln | Asp | Arg | Cys | Glu | Gln | Thr | Cys | Val | Asn | Ser | Pro | Gly | Ser | Tyr | Thr |
|     |     |     | 245 |     |     |     | 250 |     |     |     |     | 255 |     |     |     |
| Cys | His | Cys | Asp | Gly | Arg | Gly | Leu | Lys | Leu | Ser | Pro | Asp | Met | Asp |     |
|     |     |     | 260 |     |     |     | 265 |     |     |     |     | 270 |     |     |     |
| Thr | Cys | Glu | Asp | Ile | Leu | Pro | Cys | Val | Pro | Phe | Ser | Met | Ala | Lys | Ser |
|     | 275 |     |     |     | 280 |     |     |     |     | 285 |     |     |     |     |     |
| Val | Lys | Ser | Leu | Tyr | Leu | Gly | Arg | Met | Phe | Ser | Gly | Thr | Pro | Val | Ile |
|     | 290 |     |     |     | 295 |     |     |     |     | 300 |     |     |     |     |     |
| Arg | Leu | Arg | Phe | Lys | Arg | Leu | Gln | Pro | Thr | Arg | Leu | Leu | Ala | Glu | Phe |
| 305 |     |     |     | 310 |     |     |     | 315 |     |     |     |     |     | 320 |     |
| Asp | Phe | Arg | Thr | Phe | Asp | Pro | Glu | Gly | Val | Leu | Phe | Phe | Ala | Gly | Gly |
|     |     |     | 325 |     |     |     | 330 |     |     |     |     | 335 |     |     |     |
| Arg | Ser | Asp | Ser | Thr | Trp | Ile | Val | Leu | Gly | Leu | Arg | Ala | Gly | Arg | Leu |
|     |     |     | 340 |     |     |     | 345 |     |     |     |     | 350 |     |     |     |
| Glu | Leu | Gln | Leu | Arg | Tyr | Asn | Gly | Val | Gly | Arg | Ile | Thr | Ser | Ser | Gly |
|     |     | 355 |     |     |     | 360 |     |     |     |     | 365 |     |     |     |     |
| Pro | Thr | Ile | Asn | His | Gly | Met | Trp | Gln | Thr | Ile | Ser | Val | Glu | Glu | Leu |
|     |     | 370 |     |     |     | 375 |     |     |     |     | 380 |     |     |     |     |
| Glu | Arg | Asn | Leu | Val | Ile | Lys | Val | Asn | Lys | Asp | Ala | Val | Met | Lys | Ile |
| 385 |     |     |     | 390 |     |     |     | 395 |     |     |     |     |     | 400 |     |
| Ala | Val | Ala | Gly | Glu | Leu | Phe | Gln | Leu | Glu | Arg | Gly | Leu | Tyr | His | Leu |
|     |     |     | 405 |     |     |     | 410 |     |     |     |     | 415 |     |     |     |
| Asn | Leu | Thr | Val | Gly | Gly | Ile | Pro | Phe | Lys | Glu | Ser | Glu | Leu | Val | Gln |
|     |     |     | 420 |     |     |     | 425 |     |     |     |     | 430 |     |     |     |
| Pro | Ile | Asn | Pro | Arg | Leu | Asp | Gly | Cys | Met | Arg | Ser | Trp | Asn | Trp | Leu |
|     |     | 435 |     |     |     | 440 |     |     |     |     | 445 |     |     |     |     |
| Asn | Gly | Glu | Asp | Ser | Ala | Ile | Gln | Glu | Thr | Val | Lys | Ala | Asn | Thr | Lys |
|     | 450 |     |     |     | 455 |     |     |     |     | 460 |     |     |     |     |     |
| Met | Gln | Cys | Phe | Ser | Val | Thr | Glu | Arg | Gly | Ser | Phe | Phe | Pro | Gly | Asn |
| 465 |     |     |     | 470 |     |     |     | 475 |     |     |     |     |     | 480 |     |
| Gly | Phe | Ala | Thr | Tyr | Arg | Leu | Asn | Tyr | Thr | Arg | Thr | Ser | Leu | Asp | Val |
|     |     |     | 485 |     |     |     | 490 |     |     |     |     | 495 |     |     |     |

|   |   |   |   |   |   |   |   |   |   |   |   |   |   |   |
|---|---|---|---|---|---|---|---|---|---|---|---|---|---|---|
| Gly | Thr | Glu | Thr<br>500 | Thr | Trp | Glu | Val | Lys<br>505 | Val | Val | Ala | Arg | Ile<br>510 | Arg | Pro |
| Ala | Thr | Asp<br>515 | Thr | Gly | Val | Leu | Leu<br>520 | Ala | Leu | Val | Gly | Asp<br>525 | Asp | Asp | Val |
| Val | Ile<br>530 | Ser | Val | Ala | Leu | Val<br>535 | Asp | Tyr | His | Ser | Thr<br>540 | Lys | Lys | Leu | Lys |
| Lys<br>545 | Gln | Leu | Val | Val | Leu<br>550 | Ala | Val | Glu | Asp | Val<br>555 | Ala | Leu | Ala | Leu | Met<br>560 |
| Glu | Ile | Lys | Val | Cys<br>565 | Asp | Ser | Gln | Glu | His<br>570 | Thr | Val | Thr | Val | Ser<br>575 | Leu |
| Arg | Glu | Gly | Glu<br>580 | Ala | Thr | Leu | Glu | Val<br>585 | Asp | Gly | Thr | Lys | Gly<br>590 | Gln | Ser |
| Glu | Val | Ser<br>595 | Thr | Ala | Gln | Leu | Gln<br>600 | Glu | Arg | Leu | Asp | Thr<br>605 | Leu | Lys | Thr |
| His | Leu<br>610 | Gln | Gly | Ser | Val | His<br>615 | Thr | Tyr | Val | Gly | Gly<br>620 | Leu | Pro | Glu | Val |
| Ser<br>625 | Val | Ile | Ser | Ala | Pro<br>630 | Val | Thr | Ala | Phe | Tyr<br>635 | Arg | Gly | Cys | Met | Thr<br>640 |
| Leu | Glu | Val | Asn | Gly<br>645 | Lys | Ile | Leu | Asp | Leu<br>650 | Asp | Thr | Ala | Ser | Tyr<br>655 | Lys |
| His | Ser | Asp | Ile<br>660 | Thr | Ser | His | Ser | Cys<br>665 | Pro | Pro | Val | Glu | His<br>670 | Ala | Thr |
| Pro |   |   |   |   |   |   |   |   |   |   |   |   |   |   |   |

( 2 ) INFORMATION FOR SEQ ID NO:4:

( i ) SEQUENCE CHARACTERISTICS:
( A ) LENGTH: 676 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:4:

|   |   |   |   |   |   |   |   |   |   |   |   |   |   |   |
|---|---|---|---|---|---|---|---|---|---|---|---|---|---|---|
| Met<br>1 | Arg | Val | Leu | Gly<br>5 | Gly | Arg | Cys | Gly | Ala<br>10 | Pro | Leu | Ala | Cys | Leu<br>15 | Leu |
| Leu | Val | Leu | Pro<br>20 | Val | Ser | Glu | Ala | Asn<br>25 | Leu | Leu | Ser | Lys | Gln<br>30 | Gln | Ala |
| Ser | Gln | Val<br>35 | Leu | Val | Arg | Lys | Arg<br>40 | Arg | Ala | Asn | Ser | Leu<br>45 | Leu | Glu | Glu |
| Thr | Lys<br>50 | Gln | Gly | Asn | Leu | Glu<br>55 | Arg | Glu | Cys | Ile | Glu<br>60 | Glu | Leu | Cys | Asn |
| Lys<br>65 | Glu | Glu | Ala | Arg | Glu<br>70 | Val | Phe | Glu | Asn | Asp<br>75 | Pro | Glu | Thr | Asp | Tyr<br>80 |
| Phe | Tyr | Pro | Lys | Tyr<br>85 | Leu | Val | Cys | Leu | Arg<br>90 | Ser | Phe | Gln | Thr | Gly<br>95 | Leu |
| Phe | Thr | Ala | Ala<br>100 | Arg | Gln | Ser | Thr | Asn<br>105 | Ala | Tyr | Pro | Asp | Leu<br>110 | Arg | Ser |
| Cys | Val | Asn<br>115 | Ala | Ile | Pro | Asp | Gln<br>120 | Cys | Ser | Pro | Leu | Pro<br>125 | Cys | Asn | Glu |
| Asp | Gly<br>130 | Tyr | Met | Ser | Cys | Lys<br>135 | Asp | Gly | Lys | Ala | Ser<br>140 | Phe | Thr | Cys | Thr |
| Cys<br>145 | Lys | Pro | Gly | Trp | Gln<br>150 | Gly | Glu | Lys | Cys | Glu<br>155 | Phe | Asp | Ile | Asn | Glu<br>160 |
| Cys | Lys | Asp | Pro | Ser<br>165 | Asn | Ile | Asn | Gly | Gly<br>170 | Cys | Ser | Gln | Ile | Cys<br>175 | Asp |

| | | | | | | | | | | | | | | | |
|---|---|---|---|---|---|---|---|---|---|---|---|---|---|---|---|
| Asn | Thr | Pro | Gly 180 | Ser | Tyr | His | Cys | Ser 185 | Cys | Lys | Asn | Gly 190 | Phe | Val | Met |
| Leu | Ser | Asn 195 | Lys | Lys | Asp | Cys | Lys 200 | Asp | Val | Asp | Glu 205 | Cys | Ser | Leu | Lys |
| Pro | Ser 210 | Ile | Cys | Gly | Thr | Ala 215 | Val | Cys | Lys | Asn | Ile 220 | Pro | Gly | Asp | Phe |
| Glu 225 | Cys | Glu | Cys | Pro | Gly 230 | Tyr | Arg | Tyr | Asn 235 | Leu | Lys | Ser | Lys | Ser 240 | |
| Cys | Glu | Asp | Ile | Asp 245 | Glu | Cys | Ser | Glu | Asn 250 | Met | Cys | Ala | Gln 255 | Leu | Cys |
| Val | Asn | Tyr | Pro 260 | Gly | Gly | Tyr | Thr | Cys 265 | Tyr | Cys | Asp | Gly 270 | Lys | Lys | Gly |
| Phe | Lys | Leu 275 | Ala | Gln | Asp | Gln | Lys 280 | Ser | Cys | Glu | Val 285 | Val | Ser | Val | Cys |
| Leu | Pro 290 | Leu | Asn | Leu | Asp | Thr 295 | Lys | Tyr | Glu | Leu | Leu 300 | Tyr | Leu | Ala | Glu |
| Gln 305 | Phe | Ala | Gly | Val | Val 310 | Leu | Tyr | Leu | Lys | Phe 315 | Arg | Leu | Pro | Glu | Ile 320 |
| Ser | Arg | Phe | Ser | Ala 325 | Glu | Phe | Asp | Phe | Arg 330 | Thr | Tyr | Asp | Ser | Glu 335 | Gly |
| Val | Ile | Leu | Tyr 340 | Ala | Glu | Ser | Ile | Asp 345 | His | Ser | Ala | Trp | Leu 350 | Leu | Ile |
| Ala | Leu | Arg 355 | Gly | Gly | Lys | Ile | Glu 360 | Val | Gln | Leu | Lys | Asn 365 | Glu | His | Thr |
| Ser | Lys 370 | Ile | Thr | Thr | Gly | Gly 375 | Asp | Val | Ile | Asn | Asn 380 | Gly | Leu | Trp | Asn |
| Met 385 | Val | Ser | Val | Glu | Glu 390 | Leu | Glu | His | Ser | Ile 395 | Ser | Ile | Lys | Ile | Ala 400 |
| Lys | Glu | Ala | Val | Met 405 | Asp | Ile | Asn | Lys | Pro 410 | Gly | Pro | Leu | Phe | Lys 415 | Pro |
| Glu | Asn | Gly | Leu 420 | Leu | Glu | Thr | Lys | Val 425 | Tyr | Phe | Ala | Gly | Phe 430 | Pro | Arg |
| Lys | Val | Glu 435 | Ser | Glu | Leu | Ile | Lys 440 | Pro | Ile | Asn | Pro | Arg 445 | Leu | Asp | Gly |
| Cys | Ile 450 | Arg | Ser | Trp | Asn | Leu 455 | Met | Lys | Gln | Gly | Ala 460 | Ser | Gly | Ile | Lys |
| Glu 465 | Ile | Ile | Gln | Glu | Lys 470 | Gln | Asn | Lys | His | Cys 475 | Leu | Val | Thr | Val | Glu 480 |
| Lys | Gly | Ser | Tyr | Tyr 485 | Pro | Gly | Ser | Gly | Ile 490 | Ala | Gln | Phe | His | Ile 495 | Asp |
| Tyr | Asn | Asn | Val 500 | Ser | Ser | Ala | Glu | Gly 505 | Trp | His | Val | Asn | Val 510 | Thr | Leu |
| Asn | Ile | Arg 515 | Pro | Ser | Thr | Gly | Thr 520 | Gly | Val | Met | Leu | Ala 525 | Leu | Val | Ser |
| Gly | Asn | Asn 530 | Thr | Val | Pro | Phe 535 | Ala | Val | Ser | Leu | Val 540 | Asp | Ser | Thr | Ser |
| Glu 545 | Lys | Ser | Gln | Asp | Ile 550 | Leu | Leu | Ser | Val | Glu 555 | Asn | Thr | Val | Ile | Tyr 560 |
| Arg | Ile | Gln | Ala | Leu 565 | Ser | Leu | Cys | Ser | Asp 570 | Gln | Gln | Ser | His 575 | Leu | Glu |
| Phe | Arg | Val | Asn 580 | Arg | Asn | Asn | Leu | Glu 585 | Leu | Ser | Thr | Pro | Leu 590 | Lys | Ile |
| Glu | Thr | Ile | Ser | His | Glu | Asp | Leu | Gln | Arg | Gln | Leu | Ala | Val | Leu | Asp |

|     | 595 |     |     |     |     | 600 |     |     |     |     | 605 |     |     |     |
|-----|-----|-----|-----|-----|-----|-----|-----|-----|-----|-----|-----|-----|-----|-----|
| Lys | Ala | Met | Lys | Ala | Lys | Val | Ala | Thr | Tyr | Leu | Gly | Gly | Leu | Pro | Asp |
|     | 610 |     |     |     |     | 615 |     |     |     |     | 620 |     |     |     |
| Val | Pro | Phe | Ser | Ala | Thr | Pro | Val | Asn | Ala | Phe | Tyr | Asn | Gly | Cys | Met |
| 625 |     |     |     |     | 630 |     |     |     |     | 635 |     |     |     |     | 640 |
| Glu | Val | Asn | Ile | Asn | Gly | Val | Gln | Leu | Asp | Leu | Asp | Glu | Ala | Ile | Ser |
|     |     |     |     | 645 |     |     |     |     | 650 |     |     |     |     | 655 |     |
| Lys | His | Asn | Asp | Ile | Arg | Ala | His | Ser | Cys | Pro | Ser | Val | Trp | Lys | Lys |
|     |     |     | 660 |     |     |     |     | 665 |     |     |     |     | 670 |     |     |
| Thr | Lys | Asn | Ser |
|     |     | 675 |     |

DNA ENCODING A STIMULATING FACTOR FOR THE AXL RECEPTOR

FIELD OF THE INVENTION

This invention relates to the human protein encoded by the gene known as gas6. This protein functions as a stimulator and putative ligand for the axl receptor and exhibits growth factor activity.

BACKGROUND OF THE INVENTION

Interactions between serine proteases, their substrates, and their inhibitors have largely been exploited during evolution. Protease cascades are not confined to the classical blood coagulation or complement cascade. Thrombin, in addition to catalyzing fibrin polymerization, can act as a novel ligand for the recently identified thrombin receptor. Vu et al., Cell 64:1057–1066 (1991). The receptor is a member of the seven-transmembrane domain receptor family that possibly mediates other known effects of thrombin, including its role as mitogen for lymphocytes and fibroblasts. Chen et al., Proc. Acad. Natl. Sci. USA 72:131–135 (1975); Chen et al., Exp. Cell. Res. 101:41–46 (1976). Hepatocyte growth factor (also known as scatter factor), which promotes cell division and epithelial morphogenesis, is similar in structure to serine proteases, having a 38% amino acid sequence identity with plasminogen, although it lacks proteolytic activity as a result of mutation of two residues in the catalytic triad. Rubin et al., Proc. Natl. Acad. Sci. USA 88:415–419 (1991); Montesano et al., Cell 67:901–908 (1991); Gherardi et al., Nature (London) 346:228 (1990); Nakamura et al., Nature (London) 342:440–443 (1989). Hepatocyte growth factor is the ligand for the c-met proto-oncogene product, a transmembrane 190-kDa heterodimer with tyrosine kinase activity that is widely expressed in normal epithelial tissues. Bottaro et al., Science 251: 802–804 (1991); Naldini et al., Oncogene 6:501–504 (1991); Di Renzo et al., Oncogene 6:1997–2003 (1991).

In analog to this finely dissected developmental system, a considerable body of evidence has pointed to a set of different proteases as prime candidates in the regulation of tumor invasion and angiogenesis. Liotta et al., Cell 64:327–336 (1991); Mignatti et al., Physiol. Rev. 73: 1–36 (1993). The activities of these proteases are strictly regulated at the levels of both gene expression and zymogen activation. Matrisian, BioEssays 7:455–463 (1992). Moreover, the activities of most of these proteases appear to be enhanced when the enzymes are cell membrane associated. Cell-bound proteases are subject to negative regulation by natural protease inhibitors. Chen, Curr. Opin. Cell. Biol. 4:802–809 (1992). Although current knowledge of protease cascades relates to tissue remodeling during tumor invasion and angiogenesis, it is likely that other cells perform similar functions. In fact, normal tissue homeostasis is dependent on balanced rates of cell division, extracellular matrix (ECM) synthesis, and degradation. Recent evidence has demonstrated a close link between cytokines and growth factors that directly modulate these three processes. It is known that the ECM acts as a reservoir for several growth factors and modulates their activities. Flaumenhaft et al., Curr. Opin. Cell Biol. 3:817–823 (1991). There is also evidence that a number of proteases are involved in growth factor mobilization from the ECM. Barr, Cell 66:1–3 (1991); Flaumenhaft et al., J. Cell Biol. 118:901–909 (1992).

To dissect the mechanism that controls growth arrest in mammalian cells, a set of six growth arrest-specific (gas) genes: which are highly expressed during serum starvation in NIH 3T3 mouse fibroblasts have been cloned. Two of these genes, referred to as gas1 and gas2, were investigated in detail for their kinetics of induction after serum starvation and density dependent inhibition. Schneider et al., Cell 54:787–793 (1988).

More recently, a third gene, gas6, has been described in detail. Manfioletti et al., Mol. and Cell. Biol. 13:4976–4985 (1993). The gas6 gene encodes a protein which has sequence similarity with protein S, a serum protein that functions as a cofactor in a protease cascade that regulates coagulation. Tissue expression analysis of gas6 suggests that the gas6 protein is more likely to function in tissues than to play a role in serum processes. The association of gas6 expression with growth arrest suggest a possible role of the gas6 protein in the regulation of the growth of cells and tissues. The mechanism of this regulation and the precise cellular processes that gas6 participates in are not defined by these studies.

In an independent effort to identify genes that control the proliferation state of cells, a research program designed to identify novel growth factors was initiated. The strategy employed was to identify receptors for which a ligand had yet to be identified ("orphan receptors"). The orphan receptor chosen was axl, a gene involved in myeloid cell proliferation. Axl was identified by two independent laboratories as a transforming gene from cells of a patient with chronic myelogenous leukemia (O'Bryan et al., Mol. and Cell. Biol., October, 1991, pages 5016–5031), or from cells of a patient with chronic myeoloproliferative disorder (Janssen et al., Oncogene 6: 2113–2120). Both laboratories identified axl due to its ability to render 3T3 (mouse fibroblast) cells tumorigenic. Thus, axl expression appears to have profound effects on the growth state of cells. Molecular analysis of the cloned axl cDNA revealed that the axl gene coded for a novel receptor tyrosine kinase. The association of axl expression with myeloid malignancies and the ability of axl to transform cells suggest that axl functions in regulating the growth status of cells. Normally, the activity of a receptor is regulated by ligand binding. Therefore, the ligand for axl may regulate growth of cells and tissues that express the receptor. Tissues that express axl are known to include bone marrow, thymus, spleen, ovary, bladder, heart and brain.

SUMMARY OF THE INVENTION

The present invention comprises isolated nucleic acid molecules encoding a human growth factor, referred to here as gas6, which is a ligand for the axl receptor. Such molecules include DNA molecules encoding the amino acid sequence of naturally occurring human gas6, as well as DNA molecules which are complementary or hybridize thereto and DNA molecules which, but for the degeneracy of the genetic code, would hybribize thereto.

The invention also includes the isolated and purified protein encoded by and expressed from such molecules, peptide fragments or derivatives produced therefrom, and antibodies directed against such proteins. Additionally, the invention provides materials, such as expression vectors, and methods for the production of the protein by expression of the nucleic acid molecules in a microorganism or other host cell and isolation of the expressed protein. The invention further encompasses compositions comprising effective amounts of the protein.

The invention also includes use of the protein to stimulate proliferation of cells which express axl. These cells include cells derived from bone marrow, which may include progenitor cells and stromal cells, and cells within tissues that are positive for axl expression, which include spleen, thymus, testes, ovary, heart, intestine and lung.

BRIEF DESCRIPTION OF THE FIGURES

FIGS. 1A–1C gives the nucleotide sequence (SEQ ID No:1) of a full cDNA clone which encodes human gas6, from nucleotide 135 to nucleotide 2171 (indicated by double lines in panels A and C).

FIGS. 2A–2E. This figure shows the results of an analysis of the protein encoded by gas6 cDNA. The diagram at the top (panel A) shows the overall organization of the predicted gas6 amino acid sequence and the relative sizes of the four regions in the protein. A comparision of the predicted amino acid sequences of human gas6 (hGas6) (SEQ ID No:2), murine gas6 (mGas6) (SEQ ID No:3), and human protein S (hProtS) (SEQ ID No:4) is shown below that in panels B-E. The designations A, B, C and D in the diagram at the top (panel A) refer to four regions present in these proteins (discussed in the Detailed Description of the Invention, below).

FIGS. 6A–6C. This figure depicts gas6 mRNA expression in various tissues and cells. The expression of hgas6 mRNA in human tissues is shown in panel A. Equal amounts (20 μg) of total RNA, estimated by ethidium bromide staining, were analyzed by Northern blotting. The upper half of panel A shows the expression of hgas6; the lower half of panel A shows the same Northern blot hybridized with the human protein S probe. The expression of gas6 mRNA in various mouse tissues is shown in panel B. Equal amounts (20 μg) of total RNA were analyzed by Northern blotting. The upper half of panel B shows the expression of hgas6, and the lower half shows the- ethidium bromide staining. The designation "L.L.C". stands for Lewis lung carcinoma. Panel C shows gas6 nRNA expression in nontransformed and single-oncogene-transformed NIH 3T3 cells grown in 0.5% FCS for forty eight hours prior to RNA isolation. Equal amounts (20 μg) of total RNA were analyzed by Northern blotting. The upper half shows gas6 mRNA expression; ethidium bromide staining is shown in the lower half.

DETAILED DESCRIPTION OF THE INVENTION

Figure 3A:
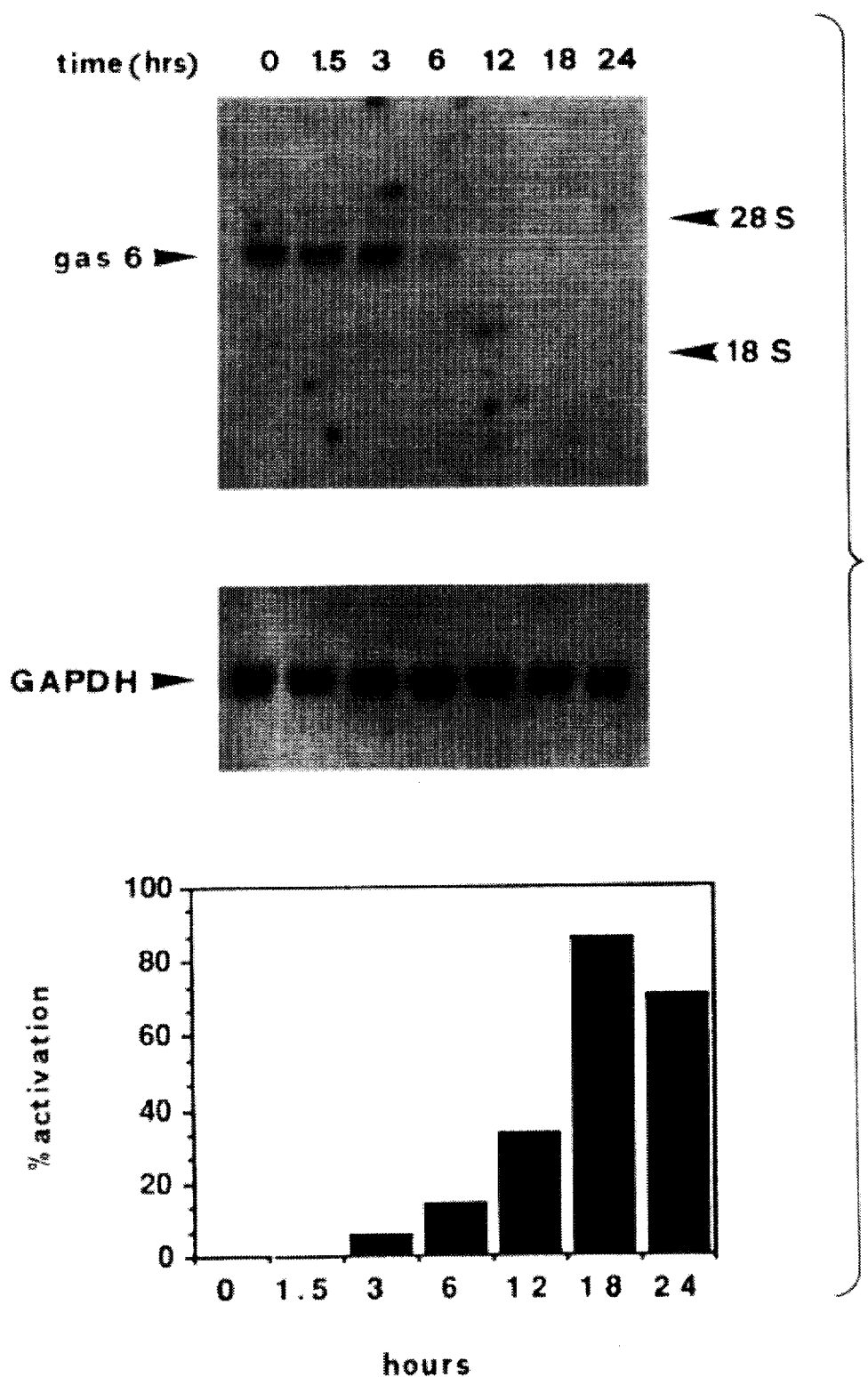
FIGS. 3A–3B. This figure shows the growth cycle regulation of gas6 gene expression in NIH 3T3 mouse fibroblast cells. RNA was extracted from NIH 3T3 cells which were arrested forty eight hours in 0.5% fetal calf serum (FCS), and at the indicated times after addition of 20% FCS (panel A) or bFGF (panel B). Equal amounts (20 μg) of total RNA were analyzed by Northern blotting. The same blots were also probed with a gapdh cDNA probe. The histograms show the relative level of DNA synthesis for each time point analyzed on the Northern blots.

The nucleotide sequence coding for gas6 protein, or portion thereof, can be inserted into an appropriate express2. on vector, i.e., a vector which contains the necessary elements for the transcription and translation of the inserted protein-coding sequence. The necessary transcriptional and translation signals can also be supplied by the native gas6 gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g. baculovirus); microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

Any of the methods previously described for the insertion of DNA fragments into a vector may be used to construct expression vectors containing chimeric gene consisting of appropriate transcriptional/translational control signals and the protein coding sequences. These methods may include in vitro recombinant DNA and synthetic techniques and in vivo recombinations (genetic recombination). Expression of a nucleic acid sequence encoding gas6 protein or peptide fragment may be regulated by a second nucleic acid sequence so that gas6 protein or peptide is expressed in a host transformed with the recombinant. DNA molecule. For example, expression of gas6 may be controlled by any promoter/enhancer element known in the art. Promoters which may be used to control gas6 expression include, but are not limited to, the SV40 early promoter region, See Bernoist and Chambon, *Nature* 290:304–310 (1981); the promoter contained in the 3' long terminal repeat of Rous sarcoma virus, Yamamoto et al., *Cell* 22:787–797 (1980); the herpes thymidine kinase promoter, Wagner et al, *Pro. Natl. Acad. Sci. U.S.A.* 78:144–145 (1981); the regulatory sequences of the metallothionine gene, Brinster et al., *Nature* 296:39–42(1982); prokaryotic expression vectors such as the β-lactamase promoter, Villa-Kamaroff et all., *Proc. Natl. Acad. Sci. U.S.A.* 75:3727–3731 (1978); or the tac promoter (DeBoer et al., *Proc. Natl. Acad. Sci. U.S.A.* 80:21–25) (1983); plant expression vectors comprising the nopaline synthetase promoter region Herrera-Estrella et al., *Nature* 303:209–21.3, or the cauliflower mosaic virus 35S RNA promoter, Gardner et al., *Nucl. Acids Res.* 9:2871 (1981); and the promoter for the photosynthetic enzyme ribulose biphosphate carboxylase, Herrera-Estrella et al., *Nature* 310:115–120 (1984); promoter elements from yeast or other fungi such as the Gal 4 promoter, the ADC (alcohol dehydrogenase) promoter, PGK (phosphoglycerol kinase) promoter, alkaline phophatase promoter, and the following animal transcriptional control region, which exhibit tissue specificity and have been utilized in transgenic animals: elastase I gene control region which is active in pancreatic acinar cells, Swift et al., *Cell* 38:639–646 (1984); Ornitz et al., *Cold Spring Harbor Symp. Quant. Biol.* 50:399– 409 (1986); MacDonald, *Hepatology* 7:425–515 (1987); insulin gene control region which is active in pancreatic beta cells, Hanahan, *Nature* 315:115–122 (1985); immunoglobulin gene control region which is active in lymphoid cells Grosschedl et al., *Cell* 38:647– 658 (1984); Adames et al., *Nature* 318:533–538 1985); Alexander et al., *Mol. Cell. Biol.* 7:1436–1444 (1987); mouse mammary tumor virus control region which is active in testicular, breast, lymphoid and mast cells Leder et al., *Cell* 45:485–495 (1986); albumin gene control region which is active in liver, Pinkert et al., *Genes and Devel.* 1:268–276 (1987); alpha-fetoprotein gene control region which is active in liver, Krumlauf et al., *Mol. Cell. Biol.* 5:1639–1648 (1985) and Hammer et al., *Science* 235:53–58 (1987); alpha 1-antitrypsin gene control region which is active in the liver, Kelsey et al., *Genes and Devel.* 1:161–171 (1987); beta-globin gene control region which is active in myeloid cells, Mogram et al., *Nature* 315:338–340 (1985) and Kollias et al., *Cell* 46:89–94 (1986); myelin basic protein gene control region which is active in oligodendrocyte cells in the brain, Readhead et al., *Cell* 48: 703–712 (1987); myosin light chain-2 gene control region which is active in skeletal muscle, Sani, *Nature* 314:283–286 (1985); and gonadotropic releasing hormone gene control region which is active in the hypothalamus, Mason et al., *Science* 234:1372–1378 (1986).

Expression vectors containing gas6 gene inserts can be identified by three general approaches: (a) DNA-DNA hybridization, (b) presence or absence of "marker" gene functions, and (c) expression of inserted sequences. In the first approach, the presence of a foreign gene inserted in an expression vector can be detected by DNA-DNA hybridization using probes comprising sequences that are homologous to an inserted gas6 gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the gas6 gene is inserted within the marker gene sequence of the vector, recombinants containing the gas6 insert can be identified by the absence of the marker gene function. In the third approach, recombinant expression vectors can be identified by assaying the foreign gene product expressed by the recombinant. Such assays can be based, for example, on the physical or functional properties of the gas6 gene product in bioassay systems.

Several methods known in the art may be used to propagate the gas6 gene. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (for example, lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered gas6 protein may be controlled. Furthermore, different host cells have characteristic and specific mechanisms for the translational and post-translational processing and modification (for example, glycosylation, gamma-carboxylation of glutamic acid residues, proteolytic cleavage) of proteins. Appropriate cell lines or host systems can be chosen to ensure the desired modification and processing of the foreign protein expressed. For instance, expression in a bacterial system can be used to produce an unglycosylated core protein product. Expression in yeast will produce a glycosylated product. Expression in mammalian cells can be used to ensure "native" glycosylation of the heterologous gas6 protein. Furthermore, different vector/host expression systems may effect processing reactions such as proteolytic cleavages or gamma-carboxylation to different extents.

The invention is explained in further detail below, which includes a description of test materials and materials and an analysis of biological results.

Cell Lines and Cell Culture Conditions. NIH 3T3 mouse fibroblasts were grown in Dulbecco's modified Eagle medium supplemented with 10% fetal calf serum (FCS), penicillin (100 U/ml), and streptomycin (100 µg/ml). For serum starvation, NIH 3T3 cells plated at $10^4/cm^2$ were shifted to 0.5% FCS for forty eight hours. Under these conditions, incubation with 50 µM bromodeoxyuridine (BUdR) for three hours resulted in labeling of less than 2% of the nuclei. For induction of DNA synthesis, fresh medium containing 20% FCS were added to growth-arrested cells. Cells were harvested at various times for RNA isolation. After eighteen hours of BUdR incorporation, more than 90% of the nuclei scored positive for DNA synthesis. For density-dependent inhibition, cells were plated at $10^4/cm^2$ in 10% FCS. Twenty four hours after plating, the medium was changed every two days. After four days in culture, incubation with BUdR for two hours yielded less than 1% of labeled nuclei. DNA synthesis was determined with a mouse monoclonal antibody against BUdR, as described by Brancolini et al., *J. Cell Biol.* 117:1251–1261 (1992). Human IMR90 fibroblasts were obtained form the Genetic Mutant Repository (Camden, N.J.) and grown as recommended. For serum starvation, subconfluent cells were shifted to 0.5% FCS for seventy two hours. Under these conditions, incubation with BUdR for three hours resulted in labeling of less than 3% of the nuclei. DNA synthesis was induced as described above; after eighteen hours of BUdR incorporation, more than 45% of the nuclei stained positive. Basic fibroblast growth factor (bFGF) was supplied by C. Grassi-Farmitalia, Milano, Italy, and used at a concentration of 100 ng/ml.

RNA Preparation and Northern (RNA) Blotting Analysis. For extraction of total RNA from cells, the cultures were washed twice with phosphate-buffered saline, and lysis buffer (4M guanidine isothiocyanate, 25 mM sodium citrate, 0.1M 2-mercaptoethanol, 0.5% N-laurylsarcosine) was added. RNA from mouse or human tissues was extracted by disrupting the tissue in lysis buffer with a Polytron homogenizer, and RNA was then isolated using the procedure described by Chomczynsky et al., *Anal. Biochem.* 162:156–159 (1987). Total RNA (20 µg) was separated on 1% agarose gels containing 6.7% formaldehyde and transferred to Duralon-UV nylon membranes (Stratagene) using a 2016 Vacugene apparatus (Pharmacia). See Lehrach et al., *Biochemistry* 16: 4743–4750 (1977). RNA was cross-linked by exposure to UV light (Stratalinker, from Stratagene). Hybridization was performed in 1M NaCl-1% sodium dodecyl sulfate (SDS) at 65° C., using the corresponding probes labeled with $^{32}p$ by random-primer synthesis (Pharmacia).

DNA Sequencing and Sequence Analysis. All DNA fragments, obtained by using appropriate restriction enzymes, were subcloned in the Bluescript KS+ plasmid (Stratagene). Plasmid and lambda DNAs were isolated and sequenced with the T7 sequencing Kit (Pharmacia). See Del Sal et al., *BioTechniques* 7:514–520 (1989) . The sequence of the hgas6 cDNA clone was obtained by using the EMBL-ALF sequencer. Specific synthetic oligonucleotides were also used as primers for the sequencing reactions.. The sequence of each nucleotide was determined three times on average, and the entire sequence was read on both strands. Sequence analysis was performed by using the Intelligenetics software package.

Cloning of Human Gas6 Gene. The murine gas6 clone described by Schneider et al. in Cell 54:787–793 (1988) was used to screen cDNA libraries generated from $G_0$ NIH 3T3 mouse fibroblasts and mouse kidney mRNA and cloned by an orientation-specific strategy in the lambda vector T7-T3/E-H. See also Gubler et al., *Gene* 25:263– 269 (1983); Dorssers et al., *Nucleic Acids Res.* 15:3629 (1987); and Grimaldi, et al., *Nucleic Acids Res.* 15:9608 (1987). Several full length clones were obtained and analyzed, all of which showed the same sequence and restriction pattern. The full cDNA sequence of mouse gas6 was found to be 2,556 nucleotides long, and encoding a protein of 673 amino acids. The predicted protein sequence of mouse gas6 was compared against the entire protein sequence data bank, using FastDB. Bairoch, EMBL Data Library, Heidelberg, Germany (1991). A significant homology with bovine and human vitamin K-dependent protein S emerged, with 43% identity between the 673 residues of mouse gas6 and the 677 residues of human protein S. Dahlbäck et al., *Proc. Natl. Acad. Sci. USA* 83:4199–4203 (1986); Lundwall et al., *Proc. Natl. Acad. Sci. USA* 83:6716–6720. (1986). The residue identity is 42% between mouse gas6 and the 676 residues of bovine protein S. To assess whether gas6 was the mouse homolog of human protein S or a related but different protein, a human lung fibroblast cDNA library was screened with mouse gas6. A partial cDNA clone representing the human homolog was isolated and used to screen a HeLa cDNA library, under high stringency conditions, and a full length cDNA clone was isolated and sequenced. The clone analyzed was 2,461 nucleotides long and encoded a human gas6 protein (hgas6) of 678 amino acids (FIG. 1), with 81% residue identity to mouse gas6 and 44% amino acid identity to human protein (FIG. 2). This comparison showed that hgas6 is related to, but different from, human protein S.

Both mouse gas6 and human gas6 primary structures were compared with that of human protein S. FIG. 2 shows the alignments and, for the sake of clarity, is divided into four regions (A, B, C and D). Region A (panel B) includes the amino terminus, which contains a very conserved hydrophobic stretch typically resembling a signal peptide. This structure is consistent with protein S being a secreted protein and suggests a similar property for gas6. Region A also contains the γ-carboxyglutamic acid (Gla) domain of protein S which is fully maintained in both mouse gas6 and human gas6. See Dahlbäck et al., *J. Biol. Chem.* 261:5111–5115 (1986) and Lundwall et al. *Proc. Natl. Acad. Sci. USA* 83:6716– 6720 (1986). A pair of cysteines, fully conserved in region A, are known to form disulfide bonds in the human protein S. Dahlbäck et al., *J. Biol. Chem.*, above. The Gla domain, which is present within the family of vitamin K-dependent proteins, is required for the calcium-dependent phospholipid binding that mediates the interaction of these proteins with cellular membranes. See Furie et al., *Cell* 53:505–518 (1988) and Sugo et al., *J. Bio. Chem.* 261:5116–5121 (1986). A similar Gla domain-dependent interaction of gas6 with cellular membranes may indicate a strict requirement for its compartmentalization in the regulation of axl stimulation. See Mann et al., *Ann. Rev. Biochem.* 57:915–956 (1988). Region B (panel C) is know as the thrombin-sensitive segment of protein S. Dahlbäck, *Biochem. J.* 209:837–846 (1983). A Leu-Arg-Ser span represents the two thrombin cleavage sites in protein S. The comparable amino acid spans are Met-Arg-Lys and Phe-Ala-Lys in murine gas6, or Ile-Gln-Lys and Phe-Ala-Thr in hgas6. The missing consensus may suggest that region B of gas6 is not susceptible to the proteolytic attack by thrombin required for the negative feedback loop of the coagulation cascade. See Dahlbäck, Biochem. J., above, and Suzuki et al., *J. Biochem.* (Tokyo) 94: 699–705 (1983) . It is noteworthy that this region presents the lowest degree of homology to human protein S (16% identity), relative to the other regions.

Region C (panel D) includes four epidermal growth factor (EGF)-like repeats, each containing six cysteines. See Doolittle et al., *Nature* (London) 307: 558–560 (1984) and Wharton et al., *Cell* 43:567–581 (1985). A consensus sequence for β-hydroxylation of Asp and Asn residues is contained in each of these domains, as is the case for human protein S. Stenflo et al., *Proc. Natl. Acad. Sci. USA* 84:368–372 (1987). Hydroxylated Asp and Asn play a role in the high-affinity binding of $Ca^{2+}$, as recently shown by nuclear magnetic resonance spectroscopy for the first EGF-like domain of factor IX, and are involved in high-affinity protein-protein interactions. See Handford et al., *EMBO J.* 9:475–480 (1990) and Rebay et al., *Cell* 67: 687–699 (1991) . The first EGF-like domain of gas6 is the one possessing the lowest homology (42% amino acid identity) to the corresponding domain of human protein S relative to the other EGF domains (domain II, 48% identity, domain III, 45% identity, and domain IV, 51% identity).

Region D (panel E) located at the carboxy terminus, is the most extensive in length and, like human protein S, does not show any resemblance to serine proteases. As is the case for human protein S, region D of gas6 shows similarity to human sex hormone-binding protein (SHBP) and to rat androgen-binding proteins. Baker et al., *Biochem J.* 243:293–296 (1987) and Gershagen et al., *FEBS Lett.* 220:129–135 (1987). The portion of hgas6 containing the highest amino acid identity (30%) and the minimum number of gaps with SHBP is included within amino acids 315 to 457. This similarity suggests that region D may be involved in steroid hormone binding. Other ECM components, including laminin A chain and agrin, show homology to SHBP within the same region as gas6. Beck et al., *FASEB J.* 4:148–160 (1990). However, there are no experimental data to indicate that these proteins are capable of binding steroid-derived molecules. The carboxy-terminal part of mouse gas6 has two potential glycosylation sites, at positions 417 and 488, respectively, the first being conserved also in hgas6 very near the positions of similar potential glycosylation sites found in the other two species of protein S.

In vitro Translation of hGas6. In vitro translatable hgas6 RNA was generated from the pCITE-1 vector (Novagene, Madison, Wis.), containing an RNA capping-independent translation enhancer sequence downstream of the $T^7$ polymerase promoter. pCITE-hgas6 contains a cDNA fragment from the ATG (nucleotide 135) to the end of the cidone and was cloned in pCITE in two steps. In the first step, the hgas6 cloned in pBluescript KS+ was digested with NcoI, which cuts in hgas6 at position 134, corresponding to the initial methionine, and at position 1260. The resulting fragment was then inserted in the same site of the pCITE vector. In the second step, hgas6 pBluescript KS+ was digested with SacI, which cuts at nucleotide 698 of the cDNA, and SalI, which is present in the polylinker of the plasmid 3' to the cDNA. The resulting fragment was inserted into a pCITE/NcoI-containing fragment digested with the same enzymes. The pCITE-hgas6 was then linearized with SalI, transcribed, and translated using the procedure described by Manfioletti et al., *Mol. Cell. Biol.* 10:2924–2930 (1990). For immunoprecipitation, the following procedure was used. Five microliters of the reticulocyte translation mixture were mixed with 0.1 ml of Nonidet P-40 (NP-40) buffer, composed of 50 mM triethanolamine (TEA) , pH 7.5, 0.1% NP-40 and 150 mM NaCl. The mixture was incubated for one hour on ice with anti-hgas6 affinity-purified antibody; 50 μl of a 10% (wt/vol) suspension of protein A-Sepharose (Pharmacia Fine Chemicals) were added, and incubation was prolonged for thirty minutes at 4° C. with rocking. After three washes with NP-40 buffer, the immunocomplex was resolved by SDS-polyacrylamide gel electrophoresis (SDS-PAGE). The gel was fixed in methanolacetic acid and treated for fluorography with Enlightening (E.I. DuPont De Nemours, Wilmington, Del.).

In Vivo Biosynthesis of hGas6. Human IMR90 fibroblasts were labeled under different growth conditions for three hours in 0.7 ml of methionine-free Dulbecco's modified Eagle medium containing [$^{35}$S]methionine (ICN-TRANS $^{35}$S label; 1,133 Ci/mmol) at approximately 500 μCi/ml. At the end of the labeling period, the medium was collected and supplemented with 50 mM TEA (pH 7.4), 150 mM NaCl, and 0.8% SDS (final concentrations). The cell monolayer was lysed with 0.5 ml of lysis buffer (150 mM NaCl, 50 mM TEA, pH 7.5, 0.1% NP-40) on ice for three minutes and the lysate was added to the culture supernatant with 0.8% SDS (final concentration). Both cell lysate and culture supernatant were then boiled for four minutes. After boiling, an equal volume of SDS quench buffer, composed of 150 mM NaCl, 50 mM TEA, pH 7.5, 4% Triton X-100, 1 mM phenylmethylsulfonyl fluoride, 10 μg each of aprotinin, leupeptin, antipain and pepstatin per ml was added. After clearing by centrifugation at 12,000 rpm for two minutes, the supernatants were incubated with 30 μl of normal rabbit serum for one hour, on ice. Samples were transferred to an Eppendorf tube containing 20 μl of pre-washed staphylococcal protein A and incubated at 4° C. for thirty minutes, with continuous rocking. After centrifugation for two minutes, the resulting supernatant was similarly treated once more and centrifuged for five minutes. Samples were then immunoprecipitated by incubation with the affinity-purified anti-hgas6 antibody for three hours at 4° C. with rocking, 80 μl of protein A-Sepharose (10% wt/vol) suspension were added, and incubation was continued for thirty minutes at 4° C. with rocking. Protein A-Sepharose was recovered by centrifugation, washed three times with 0.5% Triton X-100-20 mM TEA-150 mM NaCl-1 mM phenylmethylsulfonyl fluoride, and resuspended in SDS sample buffer. Immune complexes were released by boiling for five minutes and analyzed by SDS-PAGE as described above.

Figure 3B:
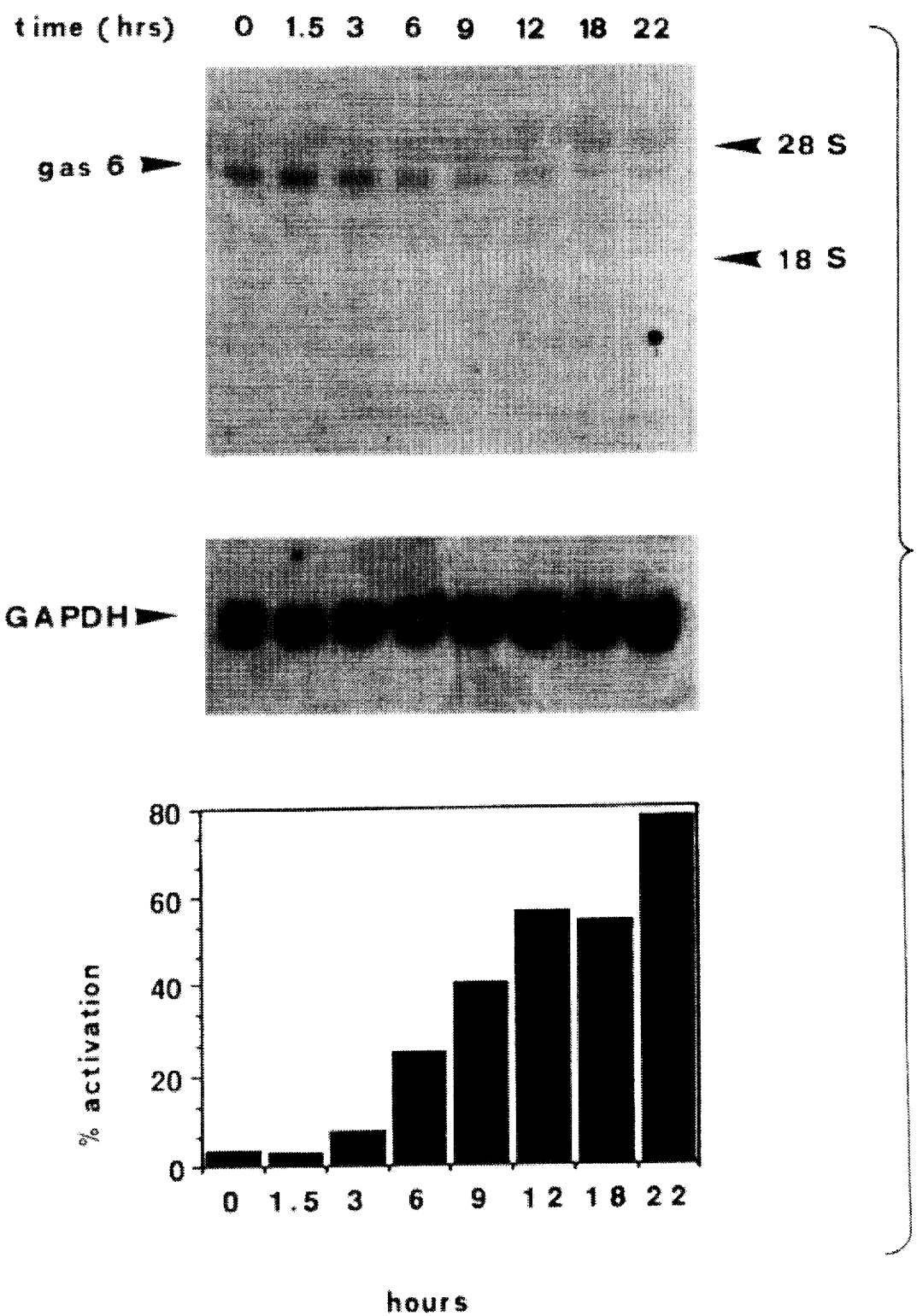

Regulation of Gas6 mRNA Expression by Serum and bFGF at Growth Arrest and During the Cell Cycle. The gene encoding gas6 belongs to a category of genes previously identified as growth arrest specific, because their expression is down-regulated after growth induction in arrested NIH 3T3 cells. FIG. 3 shows a Northern blot analysis of gas6 expression at various times after a synchronous cell division cycle induced either with FCS (panel A) or bFGF (panel B), in NIH 3T3 mouse fibroblasts arrested for forty eight hours in 0.5% FCS (time zero). The mRNA identified by the mouse gas6 cDNA is about 2.6 kb in size and is abundantly expressed at growth arrest (time zero in panel A of FIG. 3). Six hours after addition of either 20% FCS (FIG. 3, panel A) or 100 ng of bFGF per ml (FIG. 3, panel B), gas6 mRNA is already down-regulated. After six hours its level is undetectable in the case of serum stimulation, while it steadily decreases to an undetectable level after the addition of bFGF.

The same Northern blot was normalized for the amount of total RNA with the gapdh cDNA probe, which is known to remain constant throughout the growth cycle. The percentage of cells in S phase from each time point analyzed on the Northern blots is shown in the histograms in FIG. 3.

Figure 4A:
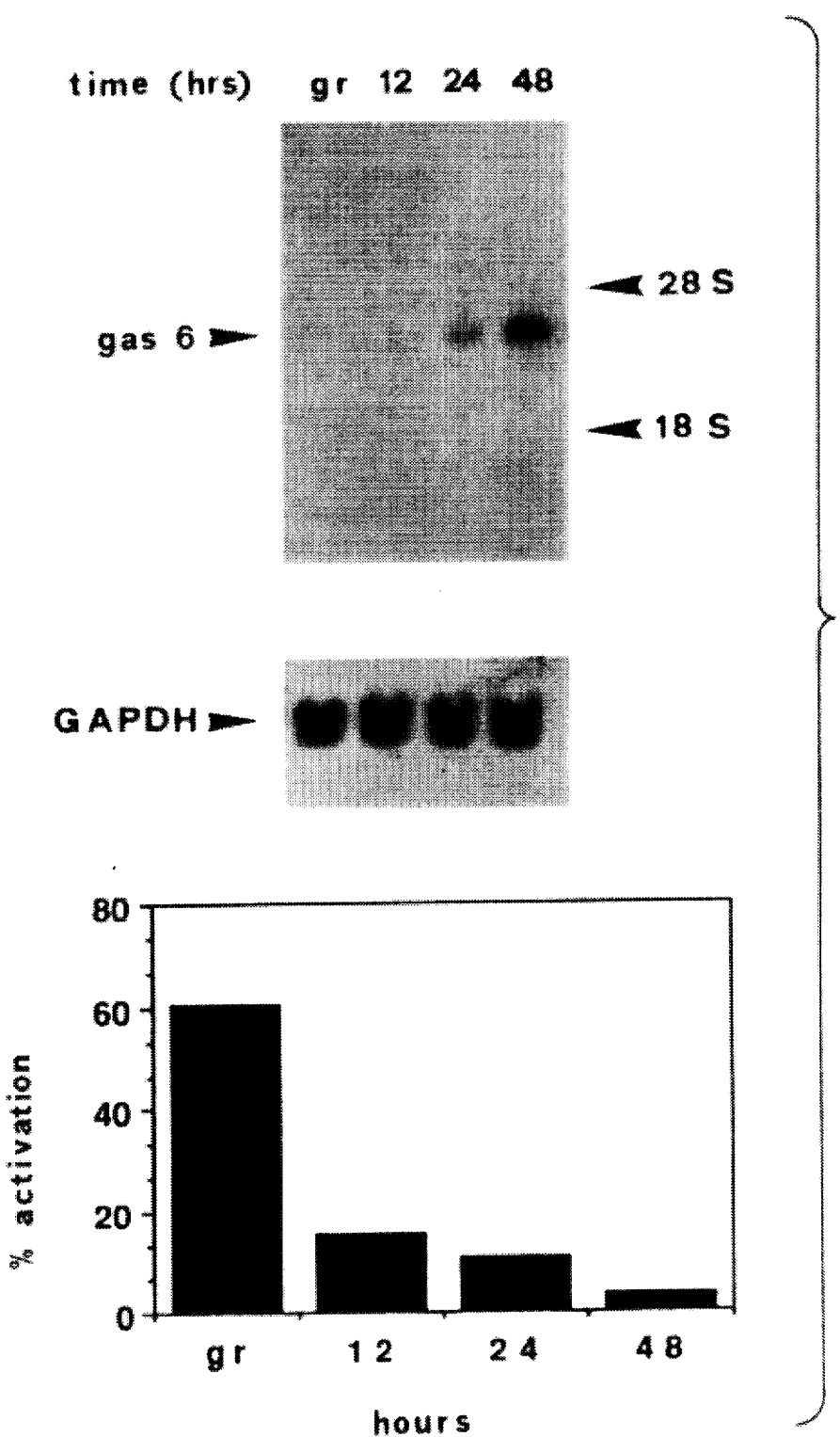
FIGS. 4A–4B. This figure shows the induction of gas6 gene expression upon serum starvation and density-dependent inhibition in NIH 3T3 mouse fibroblasts. In panel A, RNA was isolated from actively growing ("gr") NIH 3T3 cells twenty four hours after seeding in 10% FCS, and at the indicated times after serum starvation in 0.5% FCS. In panel B, RNA was isolated from actively growing ("gr") NIH 3T3 cells twenty four hours after seeding in 10% FCS, and at every two days before refeeding with fresh culture medium (containing 10% FCS). Equal amounts (20 μg) of total RNA were analyzed by Northern blotting. The same blots were also probed with the gapdh cDNA probe. The histograms show the relative level of DNA synthesis for each time point analyzed on the Northern blots.
Figure 4B:
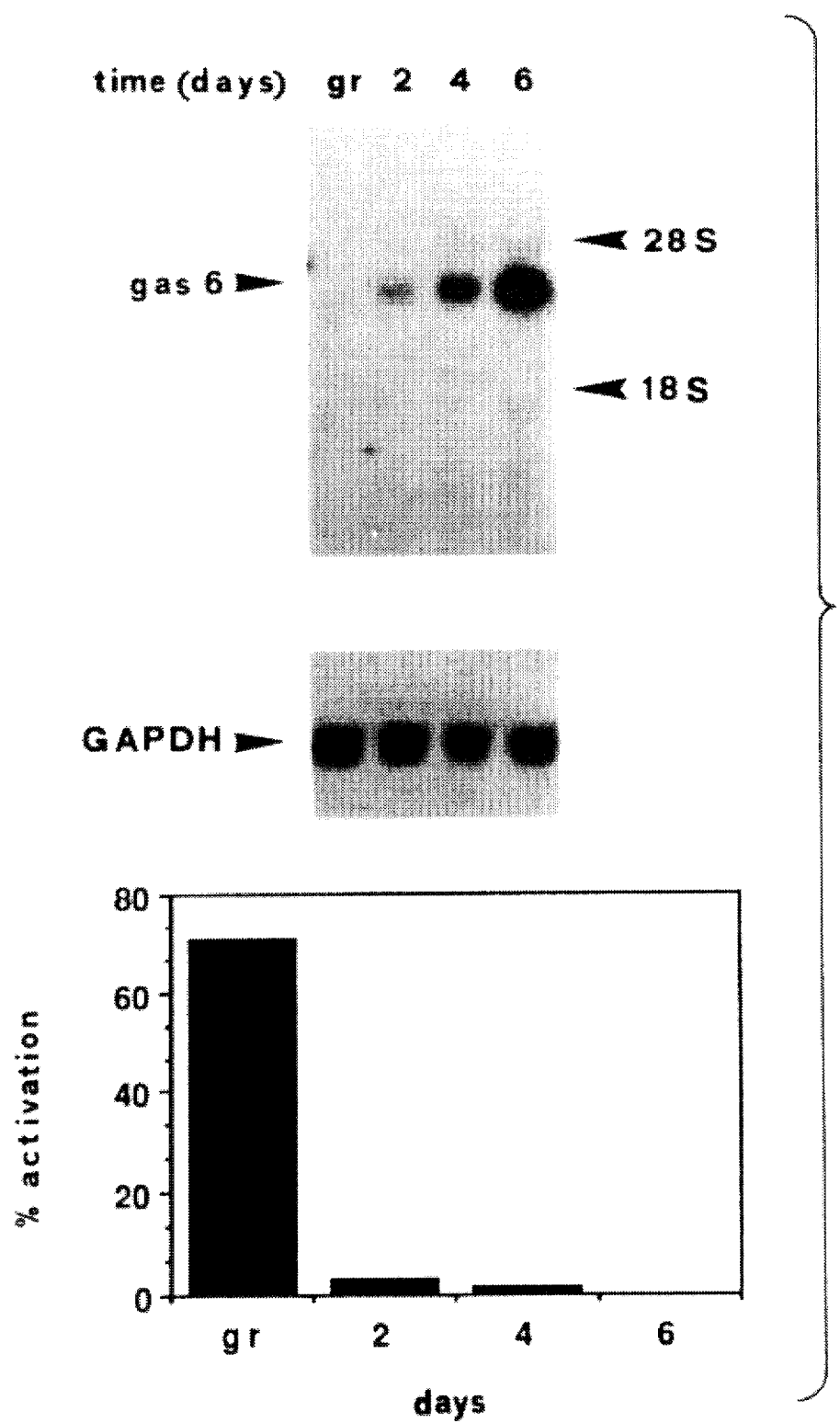

FIG. 4 shows the kinetics of gas6 mRNA accumulation during growth arrest by serum starvation (panel A) or increased cell density (panel B). Gas6 mRNA is detectable after twelve to twenty-four hours in medium containing low serum, and it reaches the highest level at forty-eight hours (FIG. 4, panel A). Normalization of RNA amount was similarly performed on the same blot with the gapdh probe, and the percentage of cells in S phase was assessed by BUdR incorporation at each time point, shown in the histograms in FIG. 4.

To analyze the expression of gas6 mRNA in relation to growth arrest induced by density-dependent inhibition, NIH 3T3 cells were seeded in 10% FCS, with the medium changed every two days. Panel B of FIG. 4 shows that gas6 mRNA is significantly increased two days after seeding, continued to accumulate up to six days. The same blot was normalized with gapdh. Under the same conditions, DNA synthesis was significantly decreased as soon as two days after seeding.

Figure 5A:
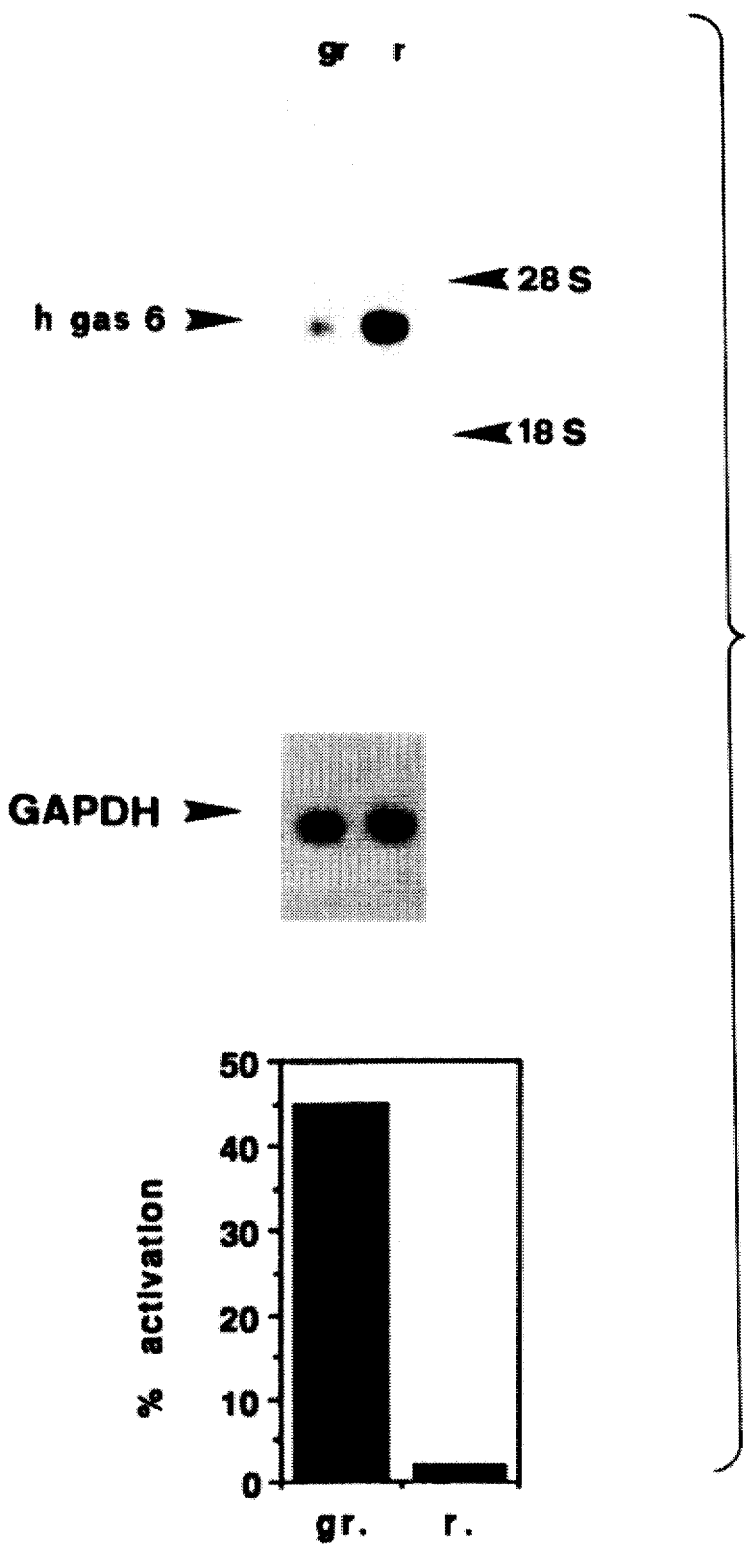
FIGS. 5A–5B. This figure shows the analysis of hgas6 mRNA expression. RNA was extracted from actively growing ("gr") and seventy two hour-serum starved human IMR90 fibroblasts (panel A) or serum-starved cells at different times after addition of 20% FCS (panel B). The same Northern blots were probed with gapdh. The histograms show the relative percentage of DNA synthesis for each time point.
Figure 5B:
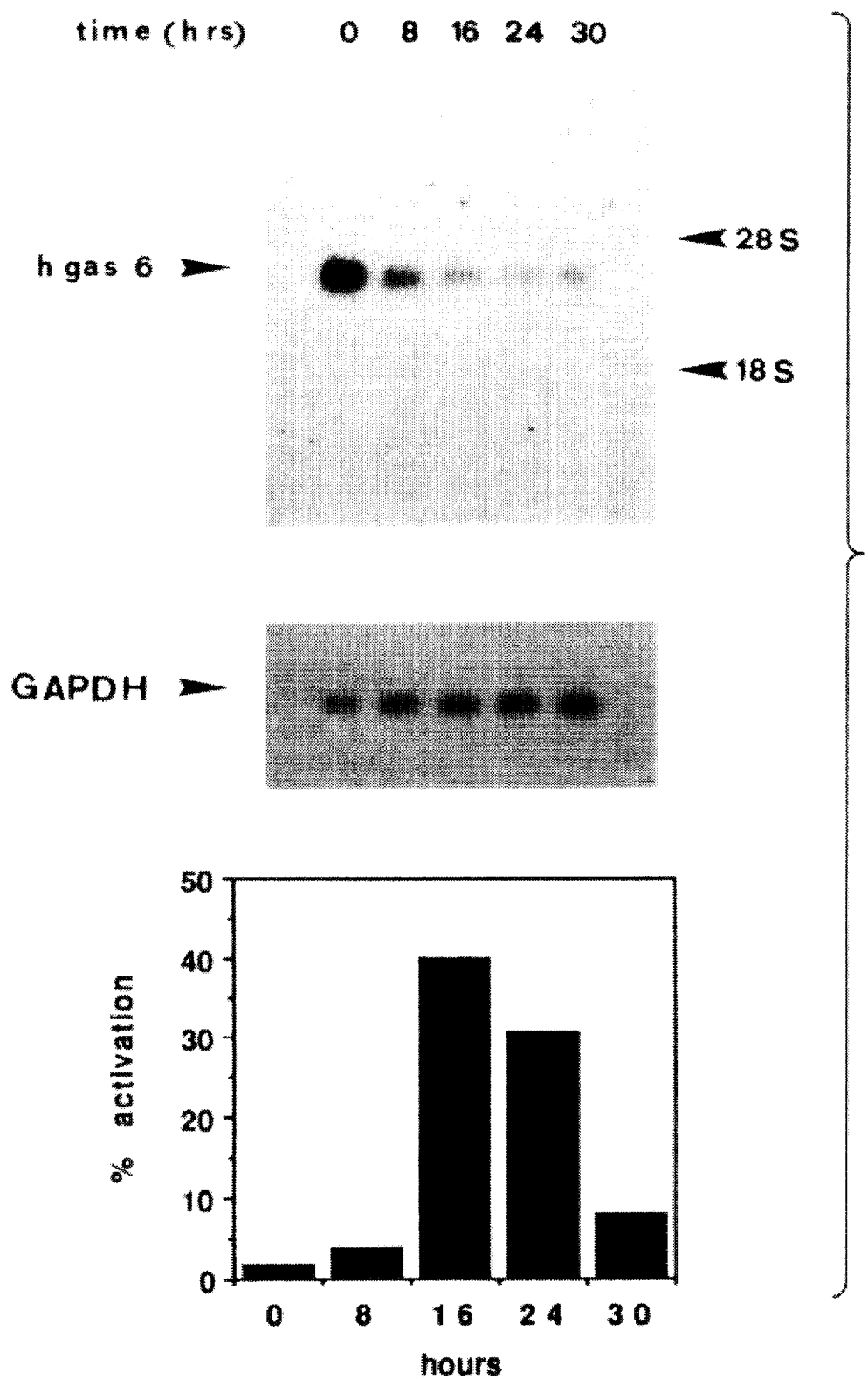

Regulation of hGas6 in Human Fibroblast Growth Arrest and During the Cell Cycle. The human cDNA clone of gas6 was used as a probe in a Northern blot analysis of total RNA extractLed from human IMR90 fibroblasts cultured under different growth conditions. Panel A of FIG. 5 shows hgas6 expression in growing and serum-starved IMR90 human fibroblasts. As can be seen, the level of hgas6 is significantly increased at growth arrest. Panel B of FIG. 5 shows hgas6 expression during a synchronous cell cycle reinduction of serum-starved IMR90 fibroblasts. As shown, hgas6 mRNA level is significantly decreased at eight hours after serum addition, reaching its lowest level at sixteen hours and maintained thereafter. The same Northern blots were probed with gapdh cDNA (FIG. 5), and the percentage of cells in S phase was also determined. Altogether, these results indicate that the expression of hgas6 mRNA in IMR90 human fibroblasts is similar to that described for mgas6 in NIH 3T3 mouse fibroblasts.

Figure 6A:
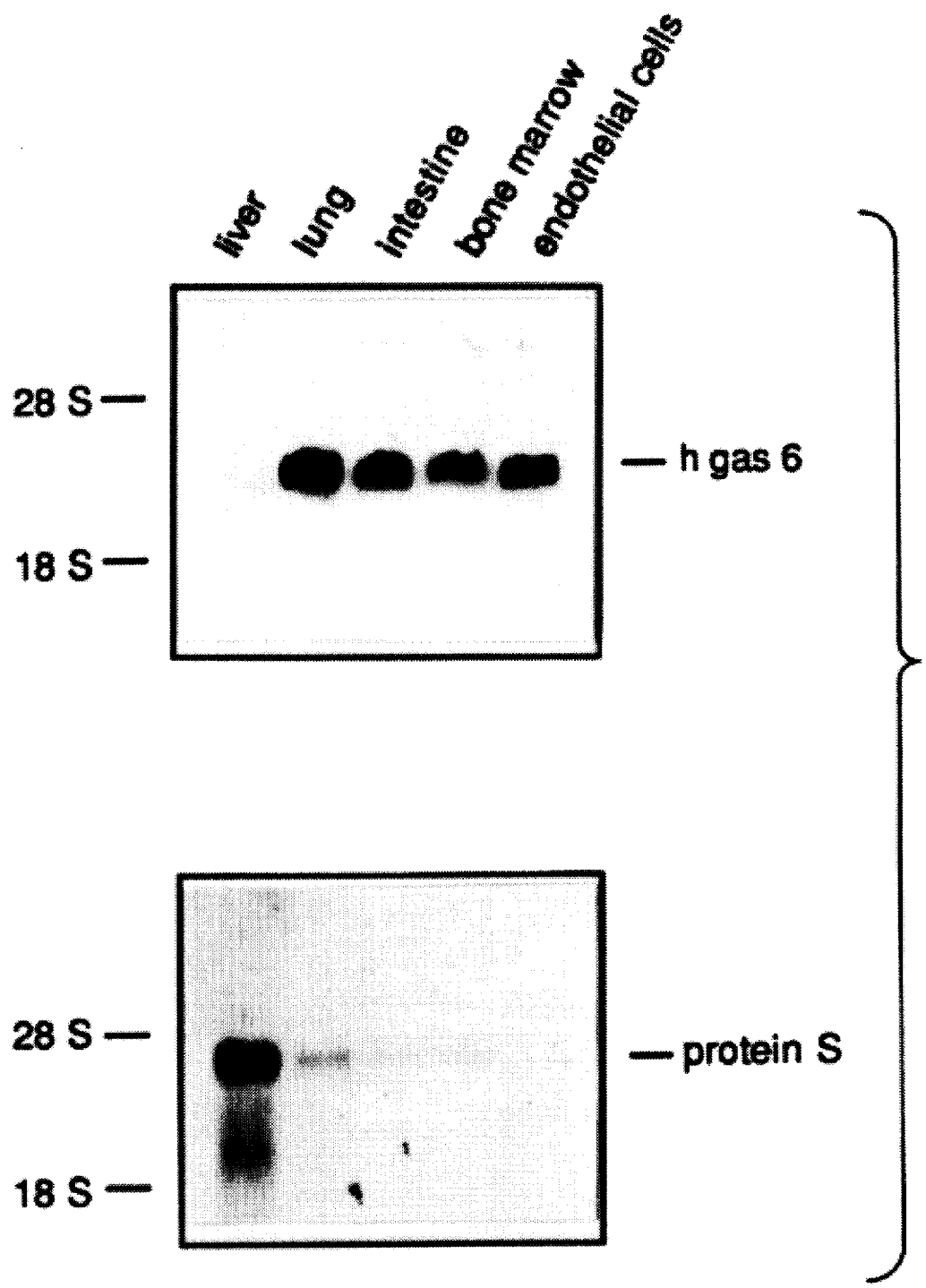

Analysis of Gas6 mRNA Expression in Tissues and Cell Lines. The total RNA isolated from different human and mouse tissues was analyzed for gas6 mRNA expression by Northern blotting. Comparable amounts of total RNA as determined by ethidium bromide staining were analyzed. Panel A of FIG. 6 shows that hgas6 mRNA, with a relative size of 2.6 kb, is expressed in all tissues analyzed at comparable levels except in the liver, where it is apparently undetectable. The same Northern blot was also probed with human protein S cDNA. The lower half of panel A in FIG. 5 shows that human protein S mRNA, with a relative size of 3.5 kb, is expressed in the liver and at a very low level in the other tissues analyzed. Panel B of FIG. 6 shows an analysis of gas6 mRNA expression in several mouse tissues, using approximately equal amounts of total RNA, as determined by ethidium bromide staining (lower half). Gas6 seemed to be expressed in many tissues analyzed, with high levels in heart, lung, stomach, and kidney tissues. RNA from a lung tumor (Lewis lung carcinoma) showed no detectable gas6 mRNA. Gas6 mRNA expression in various NIH 3T3 cell lines transformed by single oncogenes was analyzed. These lines were grown in low serum (0.5% FCS) for forty eight hours, a condition that promotes gas6 mRNA expression in nontransformed NIH 3T3 cells. Panel C of FIG. 6 shows that, under these conditions, the normal NIH 3T3 cells express a significant level of gas6 mRNA, while the single oncogene-transformed lines do not present a detectable level of gas6.

In Vitro Translation of hGas6. In vitro translatable hgas6 RNA was generated from the pCITE-1 vector (Novagene, Madison, Wis.), containing an RNA capping-independent translation enhancer sequence downstream of the T7 polymerase promoter. pCITE-hgas6 contains a cDNA fragment from the ATG (nucleotide 135) to the end of the clone and was cloned in pCITE in two steps. In the first step, the hgas6 cloned in pBluescript KS+ was digested with NcoI, which cuts in hgas6 at position 134, corresponding to the initial methionine, and at position 1260. The resulting fragment was then inserted in the same site of the pCITE vector. In the second step, hgas6 pBluescript KS+ was digested with SacI, which cuts at nucleotide 698 of the cDNA, and SalI, which is present in the polylinker of the plasmid 3' to the cDNA. The resulting fragment was inserted into a pCITE/NcoI-containing fragment digested with the same enzymes. The pCITE-hgas6 was then linearized with SalI, transcribed, and translated using the procedure described by Manfioletti et al., *Mol. Cell. Biol.* 10:2924–2930 (1990).

Polyclonal Antibody Preparation. The cDNA of hgas6 was digested with PvuII, and the resulting fragment from nucleotides 1209 to 1788 was ligated to BamHI adaptors and inserted into the BamHI site of the pAR 3038 vector, carrying the promoter of the Ψ10 gene of T7 bacteriophage. See Studier et al., *J. Mol. Biol.* 189:113–130 (1986). Expression of T7 RNA polymerase was performed by infection of host cells (*Escherichia coli* Q358) with bacteriophage λϕEG, carrying the bacteriophage T7 gene, using a multiplicity of infection of 5 to 7. Protein expression and purification were performed by the procedure of Brancolini et al., *J. Cell Biol.*, above. Rabbits were injected with 200 µg of purified bacterial hgas6 protein mixed with an equal volume of complete Freund's adjuvant. The animals were then injected with the same amount of protein in incomplete Freund's adjuvant every three weeks over a period of two months. Specific antibodies were affinity purified by using 0.5 mg of hgas6 protein covalently coupled to Affi-Prep 10 (Bio-Rad Laboratories, Cambridge, Mass.), using the procedure of Brancolini et al., above.

Figure 7B:
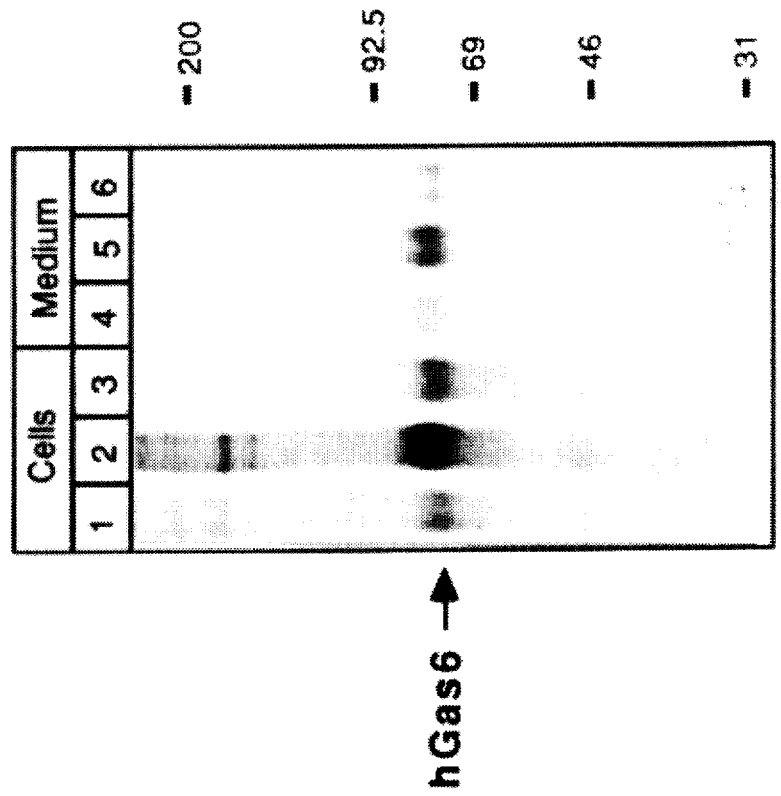
FIGS. 7A–7B. This figure presents the immunoprecipitation analysis of hgas6. Panel A shows the in vitro translation of hgas6 mRNA (lane 1), mock translation (lane 2), immunoprecipitation of the in vitro-translated hgas6 mRNA by using preimmune antiserum (lane 3) and by using anti-hgas6 affinity-purified antibodies (lane 4), and the immunoprecipitation of hgas6 from serum-starved cellular lysates of IMR90 fibroblasts (lane 5) and from the respective culture medium (lane 6) after [$^{35}$S]methionine in vivo labeling for fourteen hours. Panel B shows the immunoprecipitation analysis of hgas6 from IMR90 fibroblasts. Conditions were as follows: exponentially growing, twenty four hours after seeding in 10% FCS and three hours of [$^{35}$S]methionine labeling (lane 1, cellular lysate, anti lane 4, culture medium), serum starved, seventy two hours of 0.5% FCS incubation and three hours of [$^{35}$S]methionine labeling (lane 2, cellular lysate, anti lane 5, culture medium), and serum starved after eight hours of incubation with 20% FCS and an additional three hours or [$^{35}$S]methionine labeling (lane 3, cellular lysate, and lane 6, culture medium). Equal numbers of trichloroacetic acid-precipitable counts from the respective cellular lysate (lanes 1 to 3) or culture medium (lanes 4 to 6) were processed for immunoprecipitation.
Figure 7A:
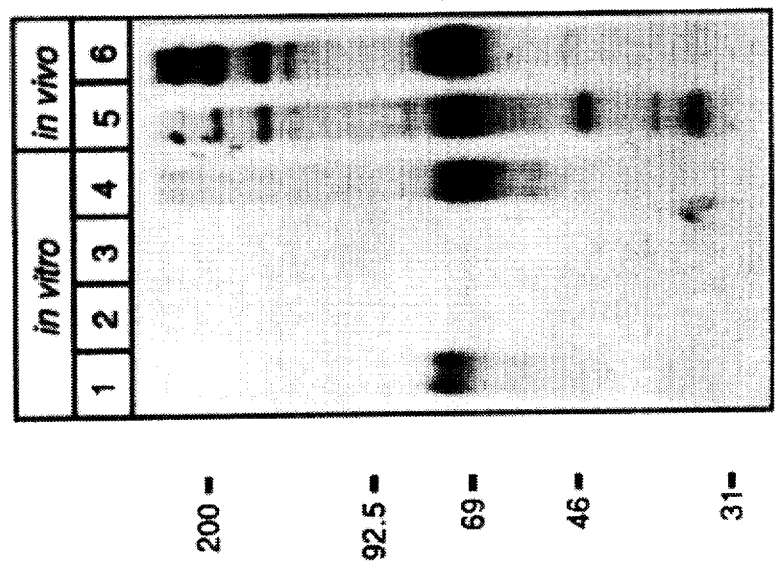

Human Gas6 Protein Analysis. To confirm that the above mentioned antibody specifically recognizes hgas6, the hgas6 primary in vitro translation product was first immunoprecipitated. For immunoprecipitation, the following procedure was used. Five microliters of the reticulocyte translation mixture were mixed with 0.1 ml of Nonidet P-40 (NP-40) buffer, composed of 50 mM triethanolamine (TEA), pH 7.5, 0.1% NP-40 and 150 mM NaCl. The mixture was incubated for one hour on ice with anti-hGas6 affinity-purified antibody; 50 μl of a 10% (wt/vol) suspension of protein A-Sepharose (Pharmacia Fine Chemicals) were added, and incubation was prolonged for thirty minutes at 4° C. with rocking. After three washes with NP-40 buffer, the immunocomplex was resolved by SDS-polyacrylamide gel electrophoresis (SDS-PAGE). The gel was fixed in methanolacetic acid and treated for fluorography with Enlightening (E. I. DuPont De Nemours, Wilmington, Del.). The protein thus obtained (FIG. 7, panel A, lane 1) had an apparent molecular mass of 7.5 kDa, as expected from the cDNA sequence. Lane 2 in panel A of FIG. 7 represents the mock control in which no RNA was added. When the total hgas6 translation was immunoprecipitated with the anti-hgas6 antibody, the same band representing hgas6 was visible (FIG. 7, panel A, lane 4), while no band is detected when pre-immune serum was used (FIG. 7, panel A, lane 3).

Human gas6 Protein Expression in IMR90 Cells. Human IMR90 fibroblasts were labeled under different growth conditions for three hours in 0.7 ml of methionine-free Dulbecco's modified Eagle medium containing [$^{35}$S]methionine (ICN-TRANS $^{35}$S label; 1,133 Ci/mmol) at approximately 500 μCi/ml. At the end of the labeling period, the medium was collected and supplemented with 50 mM TEA (pH 7.4), 150 mM NaCl, and 0.8% SDS (final concentrations). The cell monolayer was lysed with 0.5 ml of NP-40 buffer on ice for three minutes and the lysate was adjusted to 0.8% SDS (final concentration). Both cell lysate and culture supernatant were then boiled for four minutes. After boiling, an equal volume of SDS quench buffer, composed of 150 mM NaCl, 50 mM TEA, pH 7.5, 4% Triton X-100, 1 mM phenylmethylsulfonyl fluoride, 10 μg each of aprotinin, leupeptin, antipain and pepstatin per ml was added. After clearing by centrifugation at 12,000 rpm for two minutes, the supernatants were incubated with 30 μl of normal rabbit serum for one hour, on ice. Samples were transferred to an Eppendorf tube containing 20 μl of pre-washed staphylococcal protein A and incubated at 4° C. for thirty minutes, with continuous rocking. After centrifugation for two minutes, the resulting supernatant was similarly treated once more and centrifuged for five minutes. Samples were then immunoprecipitated by incubation with the affinity-purified anti-hgas6 antibody for three hours at 4° C. with rocking. 80 μl of protein A-Sepharose (10% wt/vol) suspension were added, and incubation was continued for thirty minutes at 4° C. with rocking. Protein A-Sepharose was recovered by centrifugation, washed three times with 0.5% Triton X-100-20 mM TEA-150 mM NaCl-1 mM phenylmethylsulfonyl fluoride, and resuspended in SDS sample buffer. Immune complexes were released by boiling for five minutes and analyzed by SDS-PAGE as described above. The hgas6 immunoprecipitated from cell extracts (FIG. 7, panel A, lane 5) and from conditioned medium (FIG. 7, panel A, lane 6) has an apparent molecular weight similar to that of the primary in vitro translation product. The presence of hgas6 in conditioned medium indicates that it is secreted, as suggested from the presence of a signal sequence in cDNA sequence analysis.

As shown in panel B of FIG. 6, growth arrest induced by low serum increases the level of immunoprecipitable hgas6 both in cell extracts (lane 2) and in conditioned medium (lane 5), relative to exponentially growing cells (lanes 1 and 4). To characterize hgas6 synthesis during the $G_0 \rightarrow S$ transition, 20% FCS was added for eight hours to serum-starved cells and [$^{35}$S]methionine was added for a further three-hour labeling period. The amount of hgas6 immunoprecipitated both from cell extracts (FIG. 7, panel B, lane 3) and from culture medium (FIG. 7, panel B, lane 6) is clearly decreased relative to that seen for serum-starved cells. All immunoprecipitations were normalized to contain the same amount of radioactively labeled protein. Thus, the levels of hgas6 protein are consistent with mRNA expression.

Figure 8:
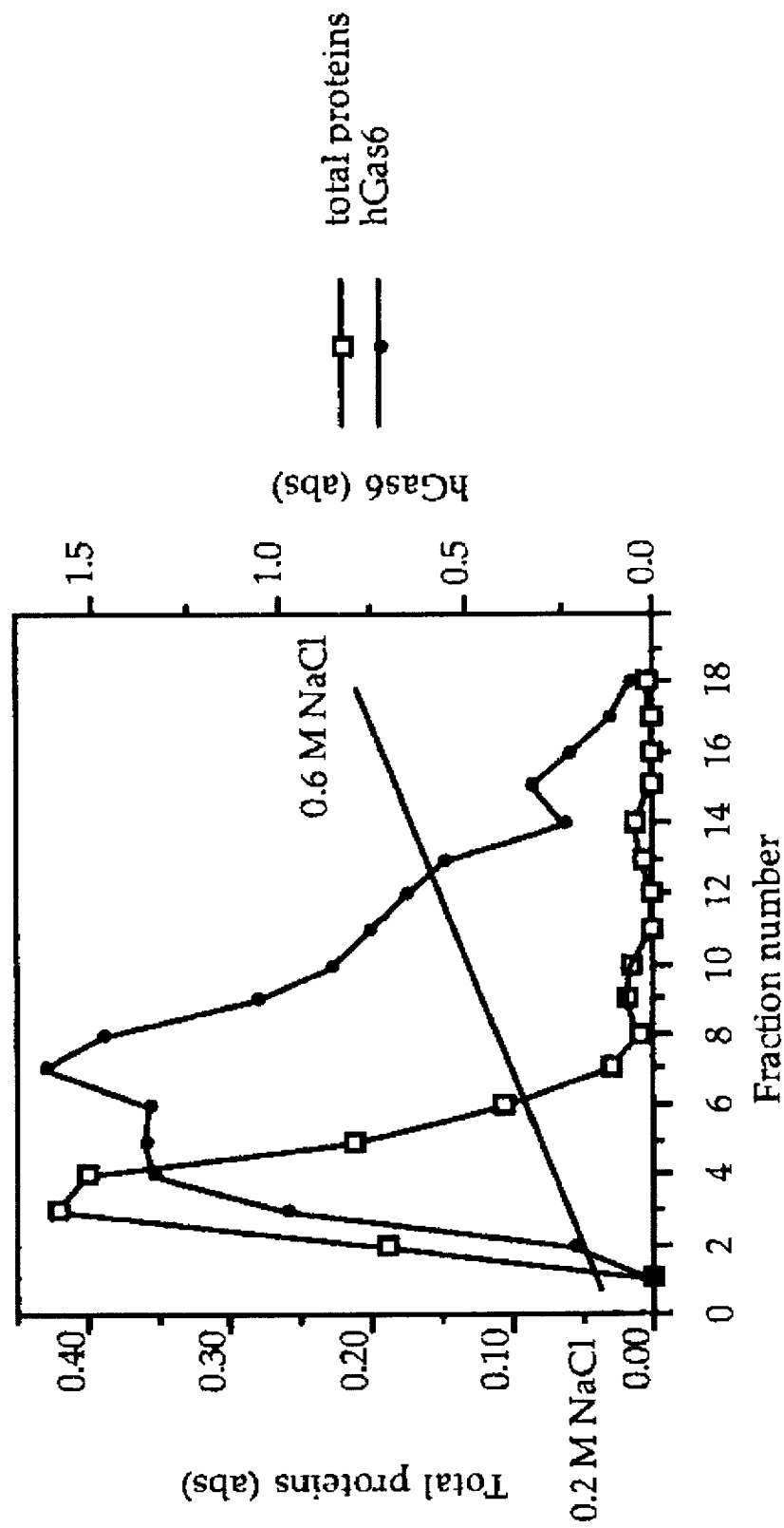
FIG. 8. This figure shows the elution profile of total protein as determined by Bradford assays (open squares), and recombinant hgas6 protein as determined by ELISA (closed circles) from COS7 supernatants fractionated on a Q Sepharose ion-exchange column. The COS7 supernatants were derived from cells which had been transfected with a hgas6 expression vector. Protein and activity were eluted from the column with a linear gradient of NaCl (0.1M to 0.6M NaCl).

Purification of Recombinant hgas6 Protein. In order to assess the role that the hgas6 protein may play in growth regulation, the recombinant protein produced in COS7 cells was partially purified by methods described for the purification of protein S. Nelson et al., *J. Biol. Chem.*, 267: 8140–8145 (1992). Supernatants from hgas6 transfected COS7 cells were diluted with three volumes of cold distilled water, and applied to a Q-Sepharose Fast Flow column (Pharmacia) that had been equilibrated with 20 mM Tris-HCl, pH 7.2, 50 mM NaCl. Proteins which bound to the column were eluted with a gradient of NaCl from 0.1M to 0.6M. FIG. 8 shows the elution of total protein, as determined by Bradford assay, and the elution of hgas6 protein, as determined by ELISA. Fractions containing the hgas6 protein were pooled, concentrated and dialysed against PBS.

Figure 9:
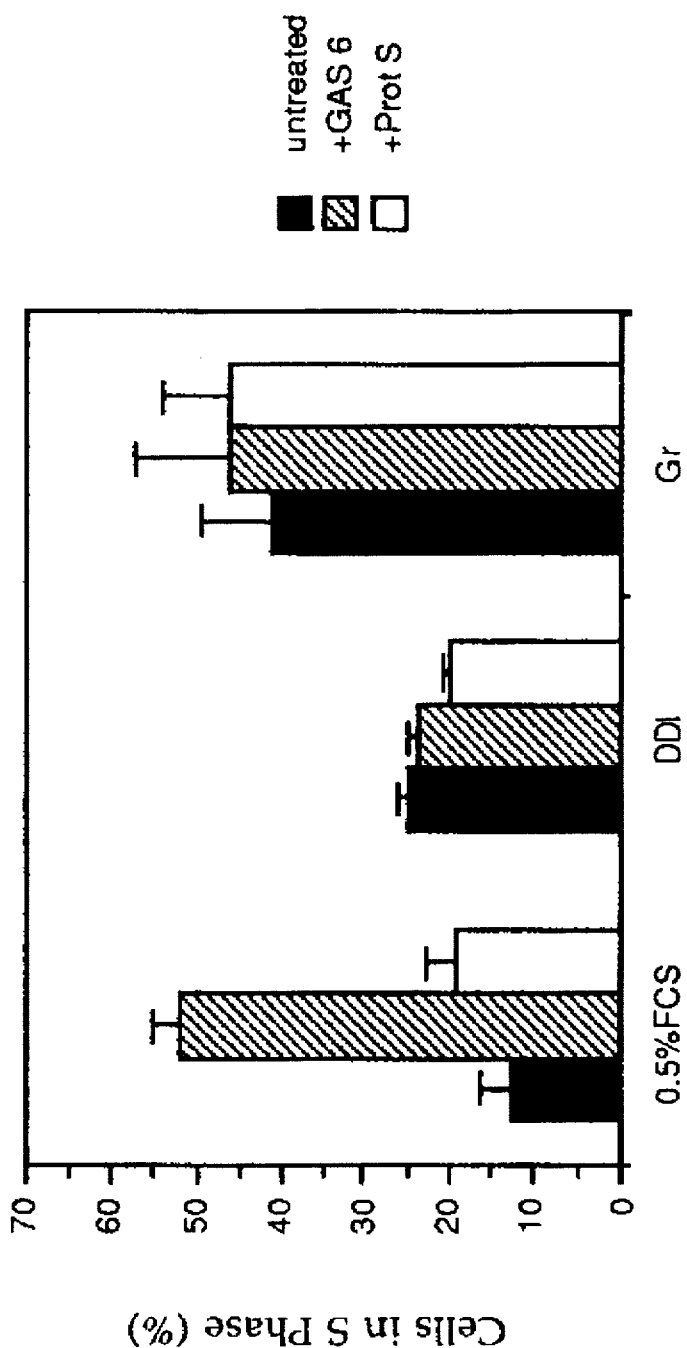
FIG. 9. This figure gives the results of an hgas6 mitogenic assay. The ability of hgas6, at a concentration of 400 μg/ml, to induce the entry of serum-depleted mouse fibroblasts (NIH 3T3) into the S phase of the cell growth cycle was assessed by measuring BrdU incorporation during twenty-four hours of gas 6 exposure. Human protein S was used as a control.

Analysis of hgas6 Growth Regulating Activities. This partially purified protein was tested for growth regulating activities on NIH 3T3 cells at an approximate concentration of 400 ng/ml. The protein was tested for activity on cells that had been growth arrested by serum starvation, cells that were growth arrested due to density dependent growth inhibition, and actively growing cells. Serum starvation was accomplished by shifting cells to media with 0.5% FCS for forty eight hours. Density arrest of growth was achieved by maintaining cells in complete media (10% FCS) for seven days. The media was changed every two days. The effect of hgas6 protein on growth was assessed by BrdU incorporation as described. Purified protein S was used as a control. As shown in FIG. 9, the partially purified hgas6 protein is able to elicit a mitogenic response from serum starved NIH 3T3 cells. In contrast, no activity is discernable on density arrested cells or on actively growing cells.

Figure 10A:
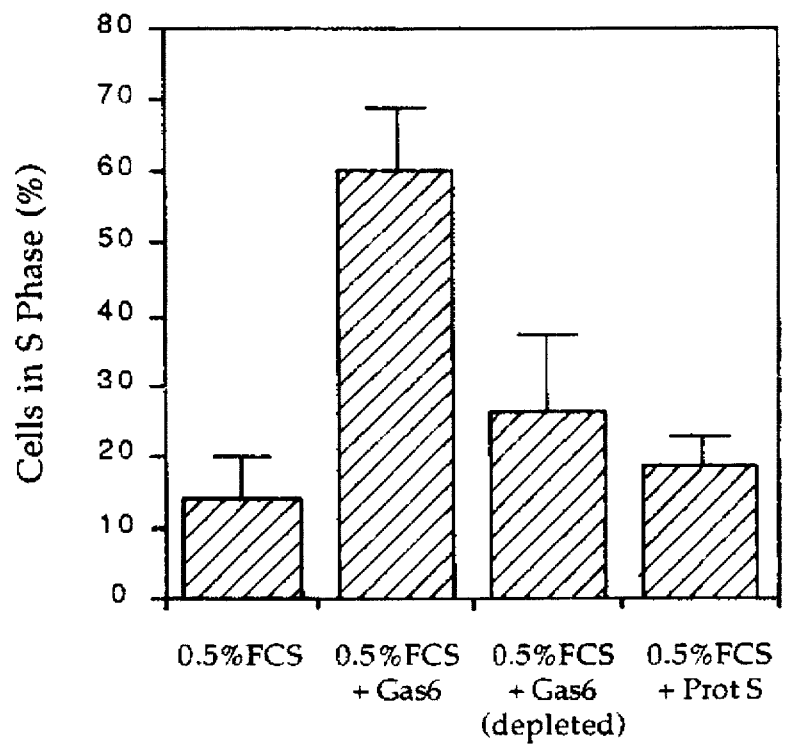
FIGS. 10A–10B. This figure gives the results of an hgas6 depletion assay, showing that an anti-hgas6 antibody column as able to deplete hgas6 transfected COS7 supernatants of growth stimulatory activity (see panel A). Depleted COS7 supernatants no longer induce DNA synthesis of low-serum arrested NIH 3T3 mouse fibroblasts as measured by BrdU incorporation (see panel B), Human protein S was again used as a control. Panel B indicates the time frame for addition of reagents, as well as the time at which cells were fixed and analyzed ("fix").
Figure 10B:
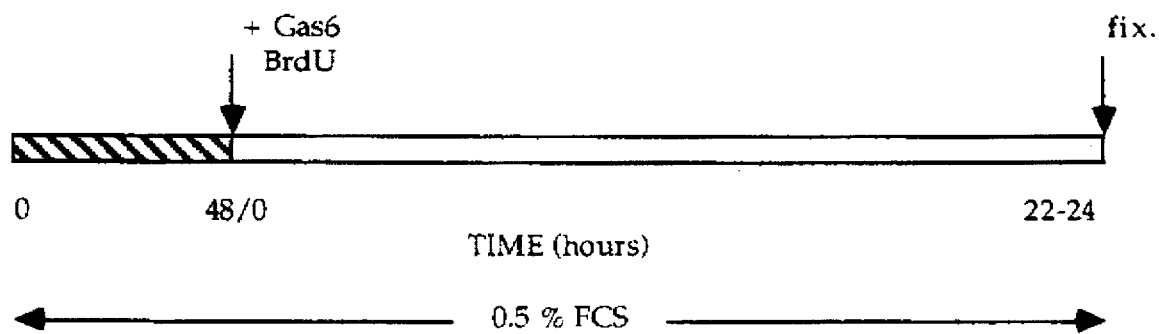

To demonstrate that the effect observed on serum starved cells is specific to the hgas6 protein, a depletion experiment was conducted. Antibodies specific to hgas6 were cross-linked to sepharose as previously described. Schneider et al., *J. Biol. Chem.* 257: 10766– 10769 (1982). Forty microliters of this antibody cross-linked sepharose was used to deplete activity from 1 ml of DMEM supplemented with 400 ng of hgas6 protein and 0.5% FCS, or the DMEM with 0.5% FCS and 400 ng of protein S. As a control, hgas6 supplemented DMEM with 0.5% FCS was incubated with mock crosslinked sepharose. After one hour at room temperature, the resin was pelleted by centrifugation, and the supernatant was tested for activity on serum starved NIH 3T3 fibroblasts. FIG. 10 shows that this depletion of hgas6 protein results in a dramatic decrease in activity as measured by BrdU incorporation. The mock crosslinked sepharose had no effect, and the protein S supplemented medium had no activity above the background level (DMEM, 0.5% FCS).

Figure 11:
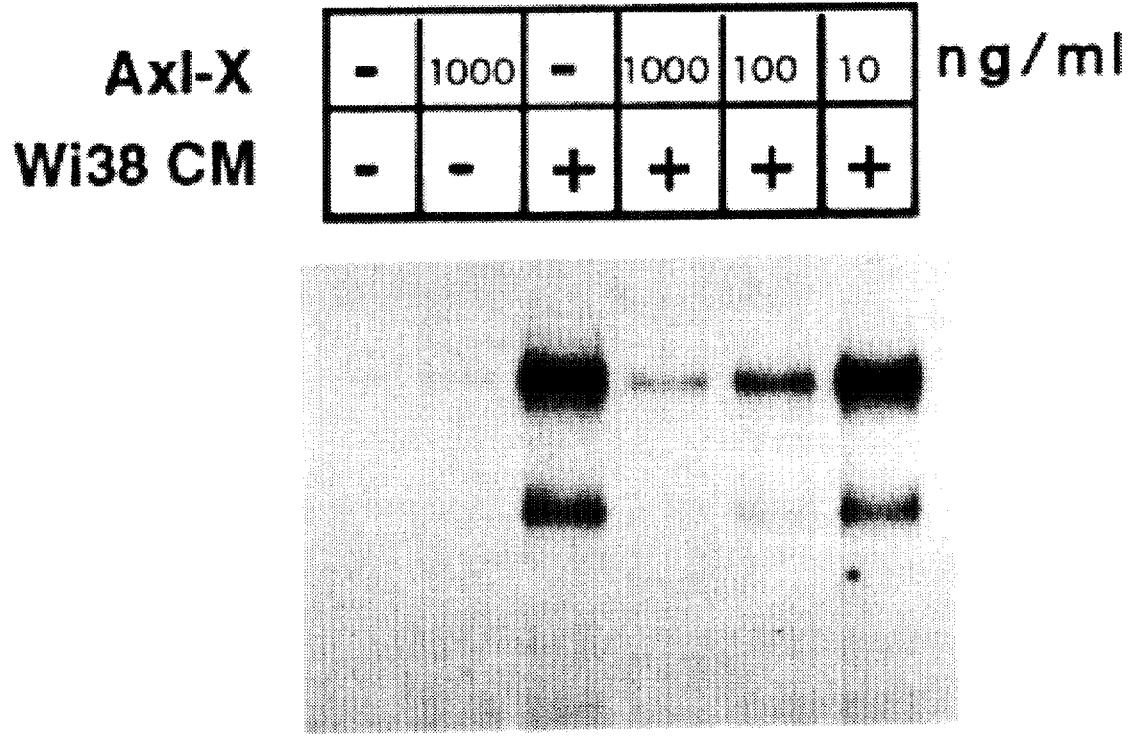
FIG. 11. This figure is the result of an anti-phosphotyrosine Western blot that depicts the increased phosphotyrosine content of axl following treatment with Wi38 conditioned medium, A172 cells were treated with control medium or Wi38 (a primary human lung fibroblast cell line) conditioned medium as indicated in the figure, Axl extracellular domain protein was added to control medium or conditioned medium at the indicated concentrations prior to addition of the media to the cells. The A172 cells were lysed and axl was immunoprecipitated as described in detail below. The phosphotyrosine content of axl was then determined by Western blotting methodologies. This figure demonstrates the presence of an axl stimulatory factor in Wi38 conditioned medium.

Identification of an Axl Stimulatory Factor. Conditioned media from a variety of cell lines was screened for axl stimulatory factors with a receptor autophosphorylation assay, as follows. Human glial blastoma cells (A172, ATCC #CRL 1620), which are known to express the axl receptor at a high level, were plated in six well plates at 5×10$^5$ cells/ well. The following day, the cells are treated for twenty minutes at 37° C. with 1 ml of test media. Media was aspirated off and 1 ml of cold lysis buffer (PBS, 1% NP-40) was added to each sample. The sample was centrifuged at 15,000 rpm for five minutes to spin down cell nuclei. The supernatant was mixed with 25 µl of protein A agarose beads and 5–10 µg of affinity purified α-axl antibody, then the resulting mixture was rotated at 4° C. for two hours. Protein A beads were pelleted and washed with lysis buffer. 20 µl of Laemmli's sample buffer with BME were added to each pellet and boiled for five minutes. The samples were separated on Tris-Glycine gels, and transferred (for Western blotting) onto a PVDF membrane (Millipore). The membrane was rinsed, then blocked with 3% BSA and 1% ovalbumin in PBST. The blot was probed with anti-phosphotyLosine (UBI, catalog no. 05-321) as the primary antibody, then goat anti-mouse horseradish peroxidase (Amersham) as the secondary antibody. The blot was developed with enhanced chemiluminescence (Amersham) and exposed to film. Two cell lines, Wi38 and Hs27, were identified as positive for axl stimulatory activity. The activity of Wi38 cell conditioned medium is demonstrated in FIG. 11. Addition of Wi38 conditioned medium results in a dramatic increase in axl phosphorylation, as demonstrated by the increase in signal detected on the anti-phosphotyrosine blot. Furthermore, addition of axl protein to the conditioned medium blocks this activity, suggesting that the activity interacts with axl directly.

Purification of the Axl Stimulatory Activity Wi38 conditioned medium was fractionated in the following manner. Approximately seventy liters of conditioned medium was loaded onto a Q-sepharose column (Pharmacia). The axl stimulatory activity was eluted with a NaCl gradient. The active fractions were pooled, and subsequently loaded onto a hydroxyapatite column (Bio-Rad). Activity was eluted with a phosphate gradient. The active fractions were pooled and loaded onto a column which contained immobilized axl extracellular domain,. Protein which bound to this axl column was eluted with 4M urea. Analysis of eluted protein revealed a 75 kilodalton protein, which was identified as gas6 by protein sequencing.

Figure 12B:
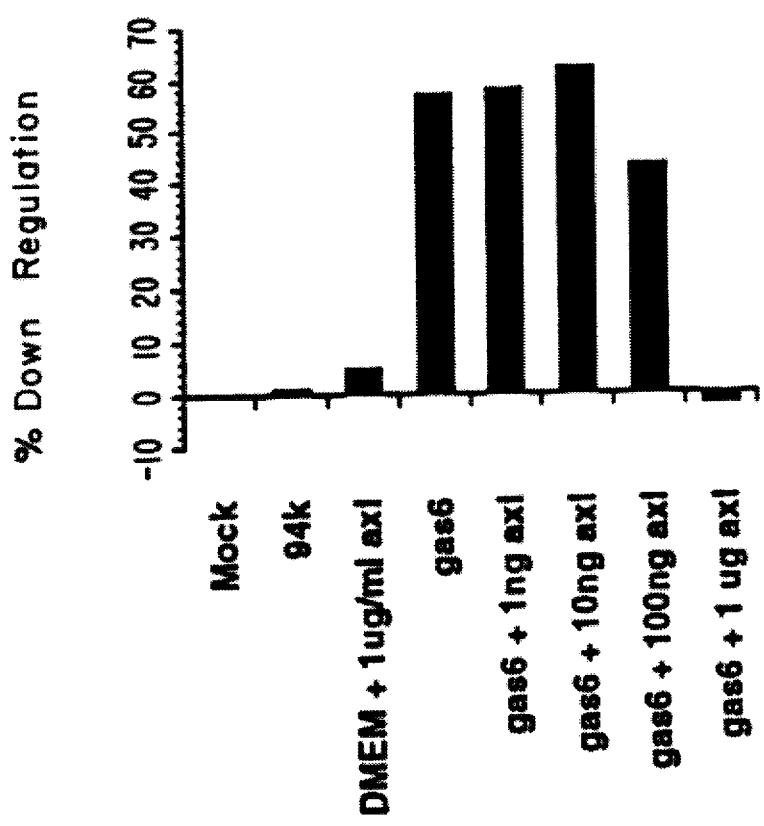
FIGS. 12A–12B. Panel A of this figure shows a Western blot analysis of the anti-phosphotyrosine content of axl receptor tyrosine kinase following treatment with COS7 cell supernatants. The result for the corresponding downregulation of axl receptor tyrosine kinase is shown below (in panel B) in the same figure. "Mock" refers to COS7 supernatants from cells transfected without DNA. "94k" refers to lipofection with an irrelevant construct (pSV-94k). DMEM+1 µg/ml sAXL is a medium control with 1 µg/ml of axl extracellular domain. Gas6 refers to COS7 supernatant from cells transfected with a gas6 expression vector, The remaining samples are gas6 transfected COS7 supernatants supplemented with the indicated amounts of axl extracellular domain.
Figure 12A:
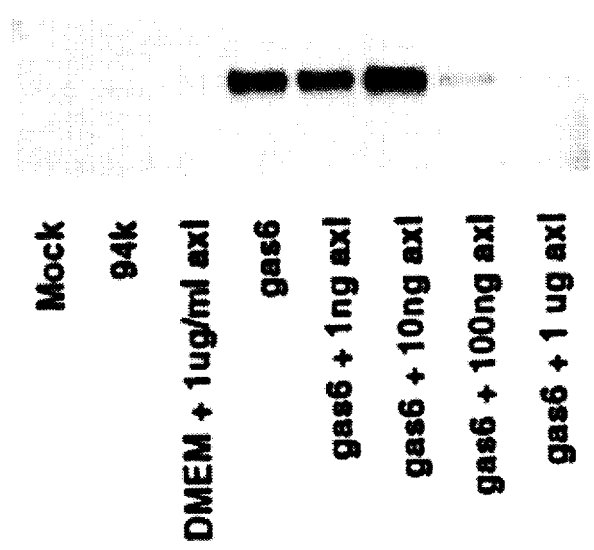

Stimulation of AXL Receptor Tyrosine Kinase. The ability of gas6 protein to react with and to stimulate the axl receptor was confirmed by measuring the ability of gas6 transfected COS cell supernatants to stimulate phosphorylation of axl receptor tyrosine kinase. COS7 cells were transfected with lipofectamine regent (Gibco-BRL) as recommended by the manufacturer. Briefly, 10 µg of DNA in 500 µl of DMEM was mixed with 40 µl of lipofectamine in 500 µl of DMEM for thirty minutes. The resultant DNA-lipofectamine complexes were diluted with 4 ml of DMEM and added to the COS cells. After four hours at 37° C., 5 ml of DMEM, 20% FCS was added. The following day, the media was replaced with DMEM, 0.5% FCS. This media was conditioned for forty eight hours, then tested for activity. COS supernatant were derived from the fermentation of COS cells which had been transfected with the gene for hgas6, an irrelevant construct (p94), or no DNA (mock). The top panel (panel A) of FIG. 12 demonstrates that the gas6-transfected COS supernatant stimulates the phosphorylation of axl, while the mock and p94 samples do not. Furthermore, this activity is abolished if soluble axl receptor is added to the COS supernatant. This indicates that gas6 does indeed have axl stimulatory activity.

Down-Regulation Of Axl Receptor. A172 cells were removed from T175 flasks by gentle scraping, then treated for one hour at 37° C. with the above described supernatants from CC, S7 cells. The cells were then washed and stained with a monoclonal antibody specific for the axl receptor labeled with phycoerythrin and staining intensities were measured by FACScan. Receptor down-regulation after ligand binding is indicated by a decrease in mean fluorescence intensity. The data are shown in the bottom panel (panel B) of FIG. 12 as percent down-regulation. The mean flourescence of the mock transfected sample was used as the control value to calculate the percent down-regulation, using the formula 100 ( 1- (Mock-Sample) +Mock) .

What is claimed is:

1. An isolated DNA molecule encoding the amino acid sequence of human gas6 (SEQ ID No:2).

2. A recombinant DNA molecule comprising the DNA molecule of claim 1 and a vector.

3. The recombinant DNA molecule of claim 2 which further comprises a promoter operably linked to said DNA molecule.

4. A host cell comprising the DNA molecule of claim 3.

5. The host cell of claim 4 which is a bacterium.

6. The host cell of claim 4 which is an animal cell.

7. A method for producing a purified human gas 6 protein having the amino acid sequence of SEQ ID NO: 2, comprising growing a microorganism or cell containing the DNA molecule of claim 1 under conditions in which the DNA molecule is expressed, and isolating the expressed protein.

* * * * *